(12) United States Patent
Coates et al.

(10) Patent No.: US 7,855,211 B2
(45) Date of Patent: Dec. 21, 2010

(54) PROTEIN KINASE INHIBITORS

(75) Inventors: David A Coates, Indianapolis, IN (US); Lawrence Mark Gelbert, Indianapolis, IN (US); John M. Knobeloch, Indianapolis, IN (US); Alfonso De Dios Magana, Carmel, IN (US); Ana De Prado Gonzalez, Madrid (ES); Miriam Filadelfa Del Prado Catalina, Madrid (ES); Maria Cristina Garcia Paredes, Madrid (ES); Eva Maria Martin De La Nava, Madrid (ES); Maria Dolores Martin Ortega Finger, Madrid (ES); Jose Antonio Martinez Perez, Madrid (ES); Ana Isabel Mateo Herranz, Madrid (ES); Carlos Perez Martinez, Madrid (ES); Concepcion Sanchez Martinez, Madrid (ES)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 12/637,789

(22) Filed: Dec. 15, 2009

(65) Prior Publication Data

US 2010/0160340 A1 Jun. 24, 2010

Related U.S. Application Data

(60) Provisional application No. 61/154,954, filed on Feb. 24, 2009.

(30) Foreign Application Priority Data

Dec. 22, 2008 (EP) .................................. 08380343

(51) Int. Cl.
*C07D 401/14* (2006.01)
*A61K 31/517* (2006.01)

(52) U.S. Cl. .................. 514/252.18; 514/275; 544/295; 544/324

(58) Field of Classification Search ................. 544/295, 544/324; 514/252.18, 275
See application file for complete search history.

(56) References Cited

U.S. PATENT DOCUMENTS

2007/0213361 A1 9/2007 Iida et al.

FOREIGN PATENT DOCUMENTS

| WO | WO 98/11095 | 3/1998 |
|----|----|----|
| WO | WO 01/60816 | 8/2001 |
| WO | WO 03/062236 | 7/2003 |
| WO | WO 2005/005426 | 1/2005 |
| WO | WO 2005/047279 | 5/2005 |
| WO | WO 2005/070900 | 8/2005 |
| WO | WO 2005/076854 | 8/2005 |
| WO | WO 2006/053109 | 5/2006 |
| WO | WO 2007/089768 | 8/2007 |
| WO | WO 2009/014637 | 1/2009 |

OTHER PUBLICATIONS

Bachmann, M. and T. Moroy, Int. J. Biochem. Cell Biol., 37(4):726-30 (2005).
Baughn, L.B. et al., Cancer Res., 66(15):7661 (2006).
Fry, D.W. et al., Mol. Cancer Ther., 3(11):1427-1437 (2004).
Grillo, M. et al., Breast Cancer Research and Treatment, 95:185-194 (2006).
Huang, S. et al., Bioorganic & Medicinal Chemistry Letters, 17:2179-2183 (2007).
Katakami, N., et al., Journal of Biological Chemistry, 279(52):54742-54749 (2004).
Kim, T. M. et al., Cancer Research, 54:605 (1994).
Lee, W.-H. et al., Science, 235:1394 (1987).
Maelandsmo, G.M. et al., British Journal of Cancer, 73:909 (1996).
Marzec, M. et al., Blood, 108(5):1744-1750 (2006).
Pogacic, V. at al., Cancer Res., 67:6916-6924 (2007).
Saab, R. et al., Mol. Cancer Ther., 5(5):1299 (2006).
Schutte, M. et al., Cancer Research, 57:3126 (1997).
Wang, L. et al., Blood, 110(6):2075-2083 (2007).

*Primary Examiner*—Deepak Rao
(74) *Attorney, Agent, or Firm*—Danica Hostettler

(57) ABSTRACT

The present invention provides a compound of formula (I):

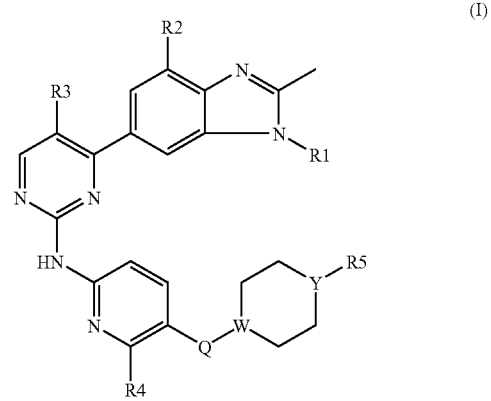

or a pharmaceutically acceptable salt thereof which is useful in the treatment of cell proliferative diseases.

23 Claims, No Drawings

PROTEIN KINASE INHIBITORS

This application claims the benefit of EP Application No. 08380343.7 filed Dec. 22, 2008, and U.S. Provisional Application No. 61/154,954 filed Feb. 24, 2009.

The highly homologous Cyclin-dependent kinases (Cdks) CDK4 and CDK6 in combination with Cyclin D are key regulators of the transition through the restriction point R between the $G_1$ (growth) and S (DNA replication) phases of the cell cycle. CDK4/6 exert their effects via phosphorylation of the retinoblastoma protein (pRb). Once phosphorylated, pRb loses its inhibitory effect on the transcription of genes promoting entry into S phase.

By contrast, specific inhibition of CDK4/6 kinase activity by the endogenous protein modulator p16$^{INK4}$ or by small molecule inhibitors results in hypophosphorylated pRb and arrest of the cells at the $G_1$ restriction point. As the primary mechanism of regulating the $G_1$ restriction point, the pathway regulated by these kinases is altered in a broad spectrum of human tumours and thus inhibition of CDK4/CDK6 in these tumours has therapeutic benefit by preventing cell division.

Pim-1 is a serine/threonine kinase that regulates diverse biological functions, including cell cycle progression, transcriptional/signal transduction pathways and apoptosis and whose expression has been linked to several cancers including haematological, prostate and oral tumours (Bachmann, M. and T. Moroy, Int. J. Biochem. Cell Biol., 2005. 37(4): p. 726-30).

Kinase inhibitors are known in the art. WO 98/11095 discloses a series of substituted 2-pyrimidineamines and describes them as kinase inhibitors, in particular the kinases p56$^{lck}$, ZAP-70 and protein kinase C. WO 98/11095 does not disclose inhibition of Cdks.

A series of 2-(pyridin-2-ylamino)-pyrido[2,3-d]pyrimidin-7-ones described as having CDK4/6 inhibitory activity are disclosed in WO 03/062236. These compounds are described as being useful in the treatment of cell proliferative disorders such as cancer and restenosis. However, the compounds are poorly soluble in aqueous solution and do not show appreciable inhibitory activity at other (non-Cdk) kinase targets.

There remains a need to provide CDK4/6 inhibitors which can be used in the treatment of cell proliferative disorders such as cancer. The present invention provides CDK4/6 inhibitors. Certain compounds of the present invention are more potent CDK4/6 inhibitors than certain compounds known in the art.

Additionally, there is a need to provide CDK4/6 inhibitors which are selective for CDK4/6 compared to other Cdks and are thus able to produce specific $G_1$ arrest when present at pharmacologically relevant concentrations. The present invention provides CDK4/6 inhibitors that are able to produce specific $G_1$ arrest when present at pharmacologically relevant concentrations.

There also remains a need to provide CDK4/6 inhibitors with improved solubility in aqueous solution. Certain compounds of the present invention have improved solubility in aqueous solution compared with certain compounds in the art.

Further, there is a need to provide CDK4/6 inhibitors which have the ability to cross the blood-brain barrier and may thus be used to treat disorders occurring within the brain, for example primary and metastatic brain tumours. Certain compounds of the present invention have the ability to cross the blood-brain barrier.

There is also a need to provide CDK4/6 inhibitors with good pharmacokinetic properties such as oral availability. Certain compounds of the present invention have improved oral availability when compared with certain compounds known in the art.

In addition, there is a need to provide kinase inhibitors that have secondary inhibitory activity at other non-Cdk kinases, for example Pim-1 kinase. Certain compounds of the present invention have dual CDK4/6 and Pim-1 kinase inhibitory activity.

The present invention provides compounds of the formula:

Formula I

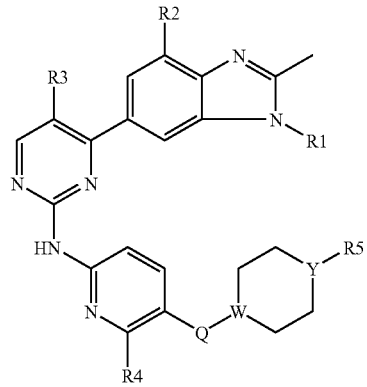

(I)

wherein,
R1 is $C_3$-$C_5$ alkyl, $C_3$-$C_5$ cycloalkyl or cyclopropyl-methyl;
R2 and R3 are H or fluorine, wherein at least one of R2 or R3 is fluorine;
R4 is H or $CH_3$;
R5 is $C_1$-$C_6$ alkyl or —NR6R7 wherein R6 and R7 are $C_1$-$C_3$ alkyl;
Q is $CH_2$, O, S or a direct bond;
and
W and Y are C or N, wherein at least one of W or Y is N and wherein when Q is O or S, W is C;
or a pharmaceutically acceptable salt thereof.

The present invention provides a pharmaceutical formulation comprising a compound of the present invention or a pharmaceutically acceptable salt thereof, and a pharmaceutically acceptable carrier, diluent, or excipient.

The present invention provides a compound of the present invention or a pharmaceutically acceptable salt thereof for use in therapy.

The present invention provides a compound of the present invention or a pharmaceutically acceptable salt thereof for use in the treatment of cancer. In particular those cancers selected from the group consisting of colorectal cancer, breast cancer, lung cancer, especially non small cell lung cancer (NSCLC), prostate cancer, glioblastoma, mantel cell lymphoma (MCL), chronic myeloid leukaemia (CML) and acute myeloid leukaemia (AML).

This invention further provides a method of treating cancer selected from the group consisting of colorectal cancer, breast cancer, lung cancer, especially non small cell lung cancer (NSCLC), prostate cancer, glioblastoma, mantel cell lymphoma, chronic myeloid leukaemia and acute myeloid leukaemia in a mammal comprising administering to a mammal in need of such treatment an effective amount of a compound of the present invention or a pharmaceutically acceptable salt thereof.

Additionally, this invention provides the use of a compound of the present invention or a pharmaceutically acceptable salt thereof for the manufacture of a medicament for the treatment of cancer. In particular those cancers are selected from the group consisting of colorectal cancer, breast cancer, lung cancer, especially non small cell lung cancer (NSCLC), prostate cancer, glioblastoma, mantel cell lymphoma, chronic myeloid leukaemia and acute myeloid leukaemia.

Furthermore, this invention provides a pharmaceutical formulation for use in therapy comprising a compound of the present invention or a pharmaceutically acceptable salt thereof and a pharmaceutically acceptable carrier, diluent, or excipient. The invention also provides a pharmaceutical formulation for treating colorectal cancer, breast cancer, lung cancer, especially non small cell lung cancer (NSCLC), prostate cancer, glioblastoma, mantel cell lymphoma, chronic myeloid leukaemia and acute myeloid leukaemia comprising a compound of the present invention or a pharmaceutically acceptable salt thereof and a pharmaceutically acceptable carrier, diluent, or excipient.

The general chemical terms used in the formulae above have their usual meanings. For example, the term "$C_3$-$C_5$ alkyl" refers to a straight or branched, monovalent, saturated aliphatic chain of three to five carbon atoms and includes, but is not limited to n-propyl, isopropyl, n-butyl, isobutyl, sec-butyl and tert-butyl.

The term $C_3$-$C_5$ cycloalkyl refers to a saturated carbon ring system containing three to five carbon atoms.

It will be understood by the skilled reader that most or all of the compounds of the present invention are capable of forming salts. The compounds of the present invention are amines, and accordingly react with any of a number of inorganic and organic acids to form pharmaceutically acceptable acid addition salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); L. D. Bighley, S. M. Berge, D. C. Monkhouse, in "Encyclopedia of Pharmaceutical Technology'. Eds. J. Swarbrick and J. C. Boylan, Vol. 13, Marcel Dekker, Inc., New York, Basel, Hong Kong 1995, pp. 453-499; S. M. Berge, et al., "Pharmaceutical Salts", *Journal of Pharmaceutical Sciences*, Vol 66, No. 1, January 1977. The hydrochloride and mesylate salts are preferred. The mesylate salt is especially preferred.

Preferably the present invention comprises compounds of Formula I wherein R1 is isopropyl, cyclopropyl, cyclopentyl or cyclopropyl-methyl. More preferably, R1 is isopropyl.

Preferably the present invention comprises compounds of Formula I wherein R2 is fluorine and R3 is hydrogen. Preferably the present invention comprises compounds of Formula I wherein R2 is hydrogen and R3 is fluorine. Most preferably both R2 and R3 are fluorine.

Preferably the present invention comprises compounds of Formula I wherein R4 is hydrogen. In an alternative, R4 is preferably methyl. Most preferably R4 is hydrogen.

Preferably the present invention comprises compounds of Formula I wherein R5 is $C_1$-$C_3$ alkyl or —NR6R7, wherein R6 and R7 are $C_1$-$C_3$ alkyl. More preferably, R6 and R7 are ethyl. More preferably R5 is $C_1$-$C_3$ alkyl. Most preferably R5 is ethyl.

Preferably the present invention comprises compounds of Formula I wherein Q is $CH_2$ or a direct bond. Most preferably Q is $CH_2$.

Preferably the present invention comprises compounds of Formula I wherein Y is N.

Preferably the present invention comprises compounds of Formula I wherein W is N.

Preferably the present invention comprises compounds of Formula I wherein both W and Y are N.

Preferred compounds of the invention include those of the formula:

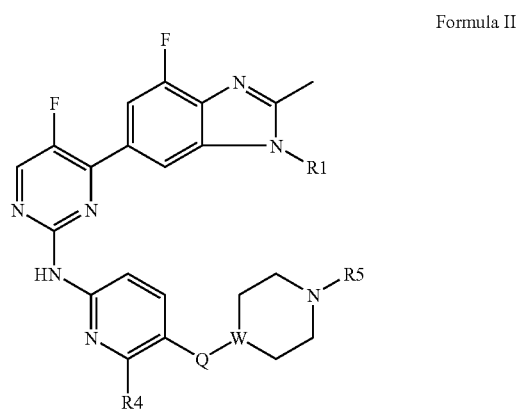

Formula II wherein:
R1 is isopropyl, cyclopropyl, cyclopentyl or cyclopropyl-methyl;
R4 is H or $CH_3$;
R5 is $C_1$-$C_3$ alkyl;
Q is $CH_2$, O or a direct bond;
and
W is C or N wherein when Q is O, W is C;

or a pharmaceutically acceptable salt thereof.

Especially preferred are the compounds exemplified herein or a pharmaceutically acceptable salt thereof. More especially preferred is the compound [5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine or a pharmaceutically acceptable salt thereof [5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine may be named in the alternative as 2-Pyrimidinamine, N-[5-[(4-ethyl-1-piperazinyl)methyl]-2-pyridinyl]-5-fluoro-4-[4-fluoro-2-methyl-1-(1-methylethyl)-1H-benzimidazol-6-yl]-.

Particularly preferred is [5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine crystalline form III, characterised by an X-ray powder diffraction pattern (CuKα radiation, λ=1.54056 Å) comprising a peak at 21.29 (2θ±0.1°) and optionally one or more peaks selected from the group comprising 11.54, 10.91, and 12.13 (2θ±0.1°). [5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine crystalline form III can be further characterised by a $^{13}$C NMR spectrum having chemical shift peaks ν(F1) [ppm] at 112.7, 127.3 and 129.4.

The compounds of the present invention are specific inhibitors of CDK4 and CDK6 and are therefore useful in the treatment of a disease or disorder characterised by abnormal cell proliferation. In particular, the compounds of the present invention are useful in the treatment of cancer.

CDK4 and CDK6 modulate their effects on the cell cycle through the phosphorylation of pRb. The compounds of the present invention, which are potent inhibitors of CDK4/6 activity and thus pRb phosphorylation, are expected to inhibit cell proliferation (and therefore tumour growth) in any cancer type where the cells are proliferating and contain a functional, intact Rb1 gene (which encodes pRb). The compounds of the invention are therefore useful in the treatment of pR+ cancers such as colorectal cancer, breast cancer, lung cancer, prostate cancer, chronic myeloid leukaemia, acute myeloid leukaemia (Fry, D. W. et al. Mol. Cancer Ther. (2004), 3(11), 1427), mantel cell lymphoma (Marzec, M. et al., Blood (2006), 108(5), 1744) ovarian cancer (Kim, T. M. et al., Cancer Research (1994), 54, 605), pancreatic cancer (Schutte, M. et al., Cancer Research (1997), 57, 3126) malignant melanoma and metastatic malignant melanoma (Maelandsmo, G. M. et al., British Journal of Cancer (1996), 73, 909) in mammals. The compounds of the invention are also expected to be useful in the treatment of rhabdomyosarcoma (Saab, R. et al., Mol. Cancer. Ther. (2006), 5(5), 1299) and multiple myeloma (Baughn, L. B. et al., Cancer Res. (2006), 66(15), 7661) in mammals. It is preferred that the mammal to be treated is a human.

Additionally, preferred compounds of the present invention exhibit the advantageous property that they are able to cross the blood-brain barrier. Such compounds are therefore able to penetrate the brain and are thus useful in the treatment of primary and metastatic brain tumours where the cells are proliferating and contain a functional, intact Rb1 gene. Examples of such pR+ brain tumours include glioblastoma as well as medulloblastoma and astrocytoma (Lee, W.-H. et al., Science (1987), 235, 1394). Temozolomide is a cytotoxic, DNA alkylating agent used for the treatment of brain tumors including glioblastoma and astrocytoma (Friedman, H. S. et al. (2000), *Clin. Cancer Res.* 6(7): 2585-97) including brain metastases from melanoma, breast cancer and NSCLC (Siena, S. et al. (2009) Annals of Oncology, doi:10.1093/annonc/mdp343). Temozolomide interacts with DNA causing chemical modification/damage (Marchesi, F., et al. (2007), *Pharmacol. Res.* 56(4): 275-87). The compounds of the present invention can be used in combination with temozolomide for the treatment of primary and metastatic pR+ brain tumours such as glioblastoma and astrocytoma, for example where such metastases are derived from melanoma, breast cancer or NSCLC.

Gemcitabine HCl, a nucleoside analogue that exhibits antitumor activity, is 2'-deoxy-2',2'-difluorocytidine monohydrochloride (β-isomer), also known as 2',2'-difluoro-2'-deoxycytidine monohydrochloride, or as 1-(4-amino-2-oxo-1H-pyrimidin-1-yl)-2-desoxy-2',2'-difluororibose. Gemcitabine HCl is described in U.S. Pat. No. 5,464,826. The structural formula is depicted below:

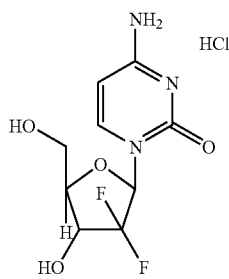

Gemcitabine HCl is effective in the treatment of non small cell lung cancer (NSCLC) (Sandler, A. and Ettinger, D. S., (1999), The Oncologist, 4, 241), pancreatic cancer (Pino, S. M. et al., (2004), Current Gastroenterology Reports, 6, 119), ovarian cancer (Pfisterer, J. et al., (2006), Journal of Clinical Oncology, 24(29), 4699) and metastatic breast cancer (Chan, S., et al. (2009), Journal of Clinical Oncology, 27(11), 1753). The compounds of the present invention can be used in combination with gemcitabine HCl for the treatment of NSCLC, pancreatic cancer, ovarian cancer and metastatic breast cancer.

The compounds of the present invention can be used in a method of treating cancer, in particular the cancers described above, in a mammal comprising administering to a mammal in need of such treatment an effective amount of a compound of the present invention. In a preferred embodiment, the compounds of the present invention can be used in a method of treating a cancer selected from the group consisting of colorectal cancer, mantel cell lymphoma, breast cancer, glioblastoma, acute myeloid leukaemia and lung cancer, especially NSCLC. In another preferred embodiment, the compounds of the present invention can be used in a method of treating a cancer selected from the group consisting of colorectal cancer, glioblastoma, acute myeloid leukaemia and lung cancer. In another preferred embodiment, a compound of the present invention can be used in a method of treating glioblastoma or astrocytoma in a mammal, comprising administering to a mammal in need thereof a therapeutically effective combination of a compound of the invention and temozolomide. In another preferred embodiment, a compound of the invention can be used in a method of treating NSCLC, pancreatic cancer, ovarian cancer or metastatic breast cancer in a mammal, comprising administering to a mammal in need thereof a therapeutically effective combination of a compound of the invention and gemcitabine HCl.

The compounds of the present invention can be used for the treatment of cancer, in particular, the cancers described above. In a preferred embodiment, the compounds of the present invention can be used for the treatment of a cancer selected from the group consisting of colorectal cancer, mantel cell lymphoma, breast cancer, glioblastoma, acute myeloid leukaemia and lung cancer, especially NSCLC. In another preferred embodiment, the compounds of the present invention can be used for the treatment of a cancer selected from the group consisting of colorectal cancer, glioblastoma, acute myeloid leukaemia and lung cancer. In another preferred embodiment, the invention provides a compound of the present invention for use in simultaneous, separate or sequential combination with temozolomide in the treatment of glioblastoma or astrocytoma. In another preferred embodiment, the invention provides a compound of the present invention for use in simultaneous, separate or sequential combination with gemcitabine HCl in the treatment of NSCLC, pancreatic cancer, ovarian cancer or metastatic breast cancer.

Furthermore, the compounds of the present invention can be used in the manufacture of a medicament for the treatment of cancer, in particular, the cancers described above. In a preferred embodiment, the compounds of the present invention can be used in the manufacture of a medicament for the treatment of a cancer selected from the group consisting of colorectal cancer, mantel cell lymphoma, breast cancer, glioblastoma, acute myeloid leukaemia and lung cancer, especially NSCLC. In another preferred embodiment, the compounds of the present invention can be used in the manufacture of a medicament for the treatment of a cancer selected from the group consisting of colorectal cancer, glioblastoma, acute myeloid leukaemia and lung cancer. In another preferred embodiment, the invention provides the use of a compound of the invention in the manufacture of a medicament for the treatment of glioblastoma or astrocytoma, wherein the medicament also comprises temozolomide or is to be administered simultaneously, separately or sequentially with temozolomide. In another preferred embodiment, the invention provides the use of a compound of the invention in the manufacture of a medicament for the treatment of NSCLC, pancreatic cancer, ovarian cancer or metastatic breast cancer, wherein the medicament also comprises gemcitabine HCl or is to be administered simultaneously, separately or sequentially with gemcitabine HCl.

There is also provided a pharmaceutical formulation for treating cancer, in particular the cancers described above comprising a compound of the present invention or a pharmaceutically acceptable salt thereof together with a pharmaceutically acceptable carrier. In a preferred embodiment, there is also provided a pharmaceutical formulation for treating a cancer selected from the group consisting of colorectal cancer, mantel cell lymphoma, breast cancer, glioblastoma, acute myeloid leukaemia and lung cancer, especially NSCLC, comprising a compound of the present invention or a pharmaceutically acceptable salt thereof together with a pharmaceutically acceptable carrier. In a preferred embodiment, there is also provided a pharmaceutical formulation for treating a cancer selected from the group consisting of colorectal cancer, glioblastoma, acute myeloid leukaemia and lung cancer, comprising a compound of the present invention or a pharmaceutically acceptable salt thereof together with a pharmaceutically acceptable carrier. In another preferred embodiment, the invention provides a pharmaceutical formulation for treating glioblastoma or astrocytoma, comprising a compound of the invention and temozolomide, together with a pharmaceutically acceptable carrier. In another preferred embodiment, the invention provides a pharmaceutical formulation for treating NSCLC, pancreatic cancer, ovarian cancer or metastatic breast cancer, comprising a compound of the invention and gemcitabine HCl, together with a pharmaceutically acceptable carrier.

The invention also provides a pharmaceutical formulation, comprising a compound of the invention or a pharmaceutically acceptable salt thereof and temozolomide, together with a pharmaceutically acceptable carrier, diluent, or excipient.

The invention also provides a pharmaceutical formulation, comprising a compound of the invention or a pharmaceutically acceptable salt thereof and gemcitabine HCl, together with a pharmaceutically acceptable carrier, diluent, or excipient.

The invention further provides a pharmaceutical formulation comprising a compound of the invention or a pharmaceutically acceptable salt thereof together with a pharmaceutically acceptable carrier and optionally other therapeutic ingredients.

Further, preferred exemplified compounds are also inhibitors of Pim-1. As noted above, Pim-1 is a serine/threonine kinase that is involved in the regulation of diverse biological functions, including cell cycle progression, transcriptional/signal transduction pathways and apoptosis and whose expression has been linked to several cancers. In particular, inhibition of Pim-1 by the small molecule inhibitor K00135 has been shown to impair the survival and clonogenic growth of a panel of human acute leukaemia cells (Pogacic, V., et al., Cancer Res. (2007). 67(14): p. 6916-24). In addition, Pim-1 has shown to be expressed in the neointima of balloon-injured rat carotid arteries and in human thoracic aortas and coronary arteries showing intimal thickening. Further, specific inhibition of Pim-1 function markedly suppressed both neointima formation after balloon injury and also the proliferation of cultured vascular smooth muscle cells (VSMCs), suggesting that Pim-1 plays a crucial role in the proliferation of such cells. The proliferation of VSMCs has been implicated in the pathogenesis of occlusive vascular diseases such as atherosclerosis and restenosis and therefore inhibition of Pim-1 is expected to suppress VSMC proliferation and thus be useful for the treatment of occlusive vascular diseases (Katakami N., et al., JBC (2004), 279(52), 54742-54749).

Accordingly, preferred compounds of the present invention, or a pharmaceutically acceptable salt thereof, can be used in a method of treating occlusive vascular disease such as atherosclerosis or restenosis in a mammal, comprising administering to a mammal in need of such treatment an effective amount of a compound of the present invention. Preferred compounds of the present invention, or a pharmaceutically acceptable salt thereof, can be used in the treatment of occlusive vascular disease such as atherosclerosis or restenosis. Furthermore, preferred compounds of the present invention, or a pharmaceutically acceptable salt thereof, can be used in the manufacture of a medicament for the treatment of occlusive vascular disease such as atherosclerosis or restenosis. There is also provided a pharmaceutical formulation for treating occlusive vascular disease such as atherosclerosis or restenosis, comprising a preferred compound of the present invention or a pharmaceutically acceptable salt thereof.

As used herein, 'h' refers to hour or hours, 'min' refers to minutes or minutes, 'Cdk' refers to cyclin dependent kinase, 'pRb' refers to retinoblastoma protein, 'MCL' refers to mantle cell lymphoma, 'AML' refers to acute myeloid leukaemia, 'CML' refers to chronic myeloid leukaemia, 'Boc' refers to N-tert-butoxycarbonyl, 'EA' refers to ethyl acetate, 'DCM' refers to dichloromethane, 'DMSO' refers to dimethylsulfoxide, 'DMA' refers to dimethylacetamide, 'THF' refers to tetrahydrofuran, 'MtBE' refers to methyl tert-butyl ether, 'TEA' refers to triethylamine, 'FBS' refers to fetal bovine serum, 'PBS' refers to phosphate buffered saline, 'BSA' refers to bovine serum albumin, 'RT' refers to room temperature, 'mpk' means milligrams per kilogram, 'po' refers to per os (oral), 'qd' means once daily dosing, 'HPLC' means high pressure liquid chromatography, 'q2d' means a single dose every 2 days, 'q2dx10' means a single dose every 2 days times 10, 'VSMC' refers to vascular smooth muscle cell and 'XRD' refers to X-ray diffraction.

The compounds of Formula I can be prepared by one of ordinary skill in the art following art recognized techniques and procedures. More specifically, compounds of Formula I can be prepared as set forth in the schemes, methods, and examples set forth below. It will be recognized by one of skill in the art that the individual steps in the following schemes may be varied to provide the compounds of Formula I. The reagents and starting materials are readily available to one of ordinary skill in the art. All substituents, unless otherwise specified, are as previously defined.

The compound names of the following preparations and examples are generated using ChemDraw® Ultra 5.0.

SCHEMES

The synthesis of compounds of formula I are illustrated in both the preparations, examples and schemes, where $R^1$, $R^2$, $R^3$, $R^4$, $R^5$, Q, W, and Y are as defined above.

Scheme 1

Compounds of formula I are prepared by palladium (0) coupling reactions as shown in scheme 1:

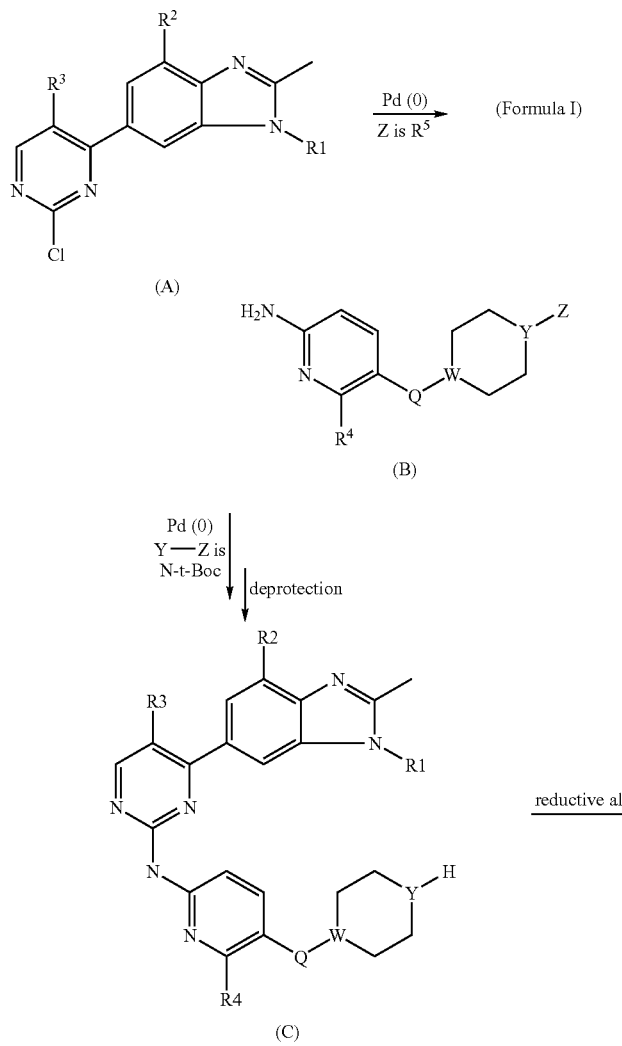

In the top reaction of scheme 1 and when Z=$R^5$, a pyrimidinyl-benzimidazole chloride (A) is reacted with a pyridinyl amine (B) in a palladium catalyzed coupling reaction to form compounds of formula I directly.

In the lower reaction of scheme 1 and when Y—Z is N-tert-butoxycarbonyl (Boc), a pyrimidinyl halide (A) is also coupled with a pyridinyl amine (B), but the Boc group is removed in strong acid to produce the free amine (C). Finally, the amine (C) is alkylated under reducing conditions to produce compounds of formula I.

Scheme 2

Preparation of pyrimidinyl-benzimidazoles (A)

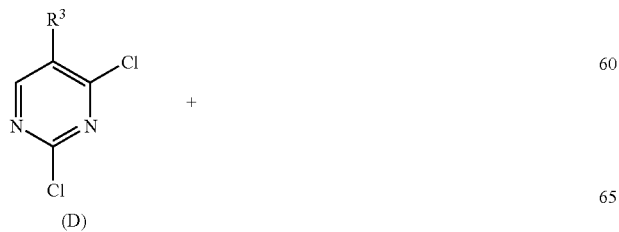

-continued

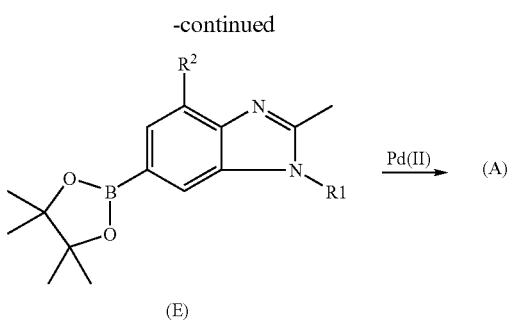

Pyrimidinyl-benzimidazoles (A) are prepared by palladium (II) catalyzed coupling reactions of commercially available pyrimidinyl dichlorides (D) and benzimidazole boronates (E).

Scheme 3
Preparation of benzimidazole boronates (E)

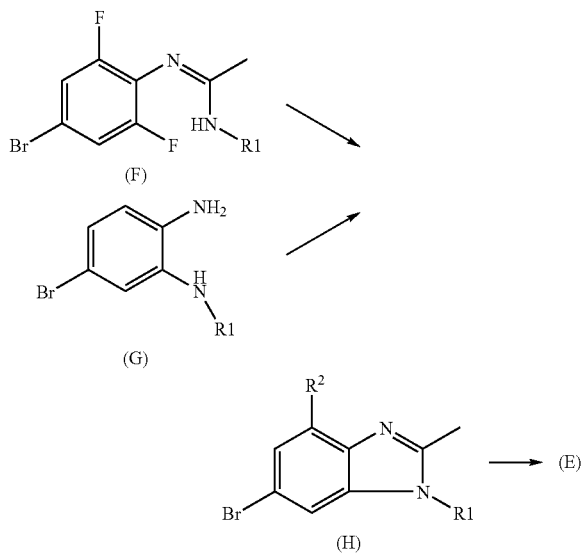

Benzimidazole boronates (E) are prepared via Pd(II) catalyzed boronylation of the bromide in benzimidazoles (H) with bis(pinacolato)diboron. Benzimidazoles (H) in turn are prepared by cyclization of the amidines (F) with potassium t-butoxide or condensation of the benzenediamines (G) with triethylorthoacetate/acetic acid.

Amidines (F) are prepared as is known by one skilled in the art of organic synthesis by condensing 4-bromo-2,6-difluorophenylamine with the mono-acetamide derivative of amines $R1-NH_2$ in the presence of phosphoryl chloride. Benzenediamines (G) are prepared in two steps as is known by one skilled in the art of organic synthesis by the displacement of the 2-position bromine in 2,4-dibromo-nitrobenzene by amines $R1-NH_2$ followed by reduction of the nitro group to an amine group.

Scheme 4
Preparation of pyridinyl amines (B), Where Q is S or O and W is C

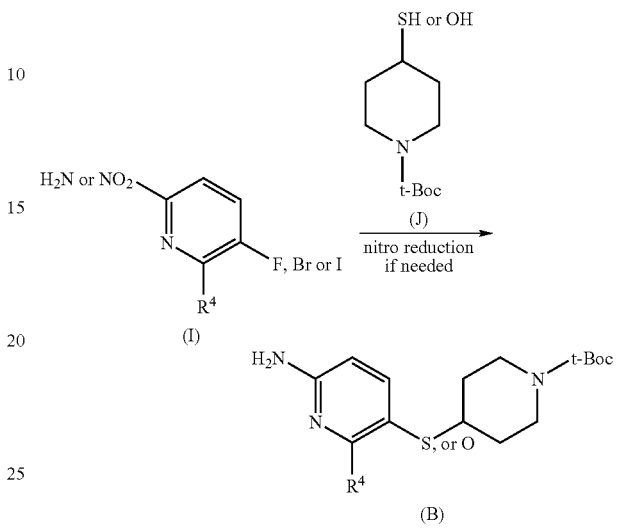

The synthesis of pyridinyl amines (B) where Q is S or O and W is C is achieved by displacement of a 5-halide in pyridine (I) by the commercially available thiol or alcohol (J). If a nitropyridine (I) is needed, the displacement product further undergoes a nitro reduction step to produce (B). It should be noted that compounds (I) are versatile reagents throughout these schemes, but only some are commercially available as pyridyl amines and some as nitropyridines. The commercially available (I) are nonetheless convertible via amine oxidation or nitro reduction reactions known in the art for the sequences described here and below.

Scheme 5
Preparation of pyridinyl amines (B), Where Q is $CH_2$

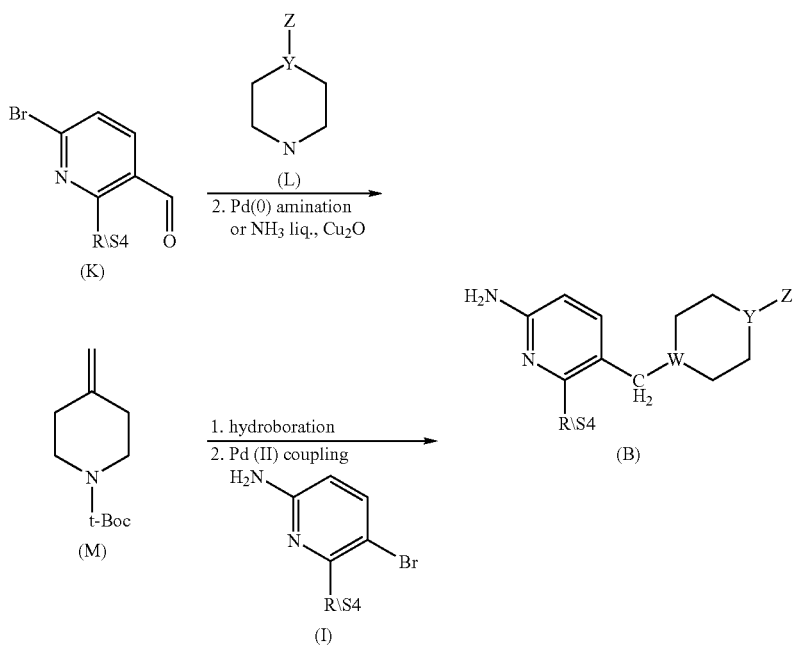

The synthesis of pyridinyl amines (B) where Q is CH₂ is achieved in two ways: 1) The commercially available carbaldehydes (K) undergo reductive amination with the free amine (L) followed by replacement of the pyridine bromide by Pd(0) catalyzed amination with lithium 1,1,1,3,3,3-hexamethyl-disilazane or liquid ammonia and cuprous oxide. 2) Commercially available 1-piperidinecarboxylic acid, 4-methylene-, 1,1-dimethylethyl ester (M) undergoes hydroboration followed by Pd (II) coupling with pyridyl amine (I).

solution of 2-amino-5-fluoropyridine (9 g) in concentrated sulfuric acid (46 mL) drop wise with an addition funnel Stir the resulting dark solution at 0° C. to RT in the bath overnight. Pour over 200 mL ice-water and extract with DCM. Wash combined organic layers with 5% aqueous solution of sodium bisulfite and dry over anhydrous sodium sulfate. Remove the solvent under vacuum and purify by silica gel column chromatography eluting with DCM to afford 7.5 g of the title compound. MS (ES⁺): m/z=143 (M+H)⁺.

Scheme 6

Preparation of pyridinyl amines (B), Where Q is a direct bond

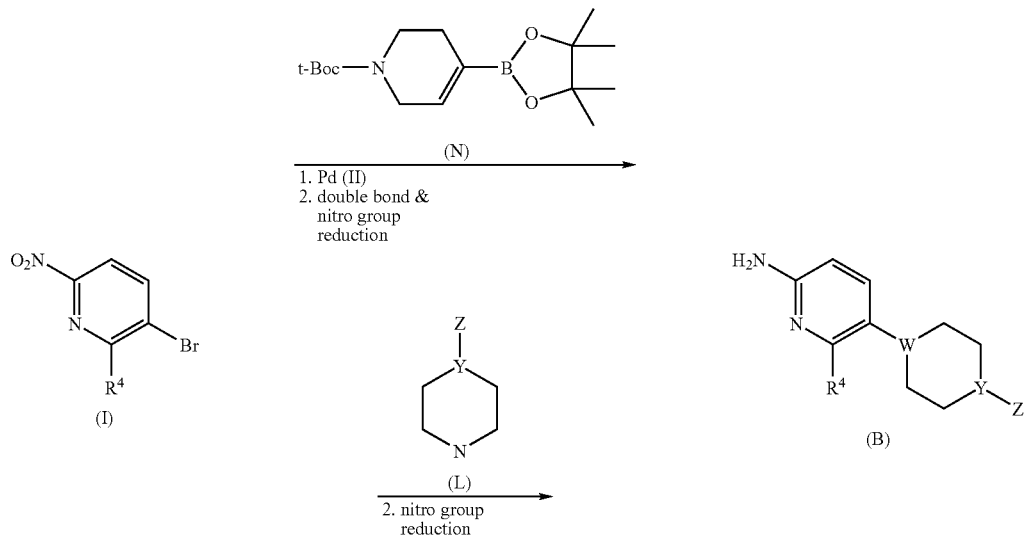

The synthesis of pyridinyl amines (B) where Q is a direct bond is achieved in two ways: 1) Commercially available 1(2H)-pyridinecarboxylic acid, 3,6-dihydro-4-(4,4,5,5-tetramethyl-1,3,2-dioxaborolan-2-yl)-, 1,1-dimethylethyl ester (N) undergoes palladium (II) coupling with nitropyridine (I) followed by reduction of both the nitro group and double bond. 2) The bromide in nitropyridine (I) is displaced by free amine (L) followed by nitro group reduction.

Preparation 1

4-(6-Amino-pyridin-3-ylsulfanyl)-piperidine-1-carboxylic acid tert-butyl ester

Add dry toluene (6.06 mL) to a mixture of 2,9-dimethyl-1,10-phenanthroline (76.52 mg), copper(I) iodide (69.27 mg), sodium tert-butoxide (475.59 mg), 4-mercapto-piperidine-1-carboxylic acid tert-butyl ester (583.5 mg), magnesium (49.10 mg) and 2-amino-5-iodopyridine (550 mg). Bubble nitrogen into the mixture with ultrasound and stir the suspension at 110° C. in a sealed tube for 24 h. Cool and filter through celite. Wash with toluene and remove the solvent under vacuum. Add hexane/EA (1/1) and filter through a celite/silica gel pad, washing twice with hexane/EA (1/1) and then EA. Remove the solvent under vacuum. Purify by silica gel column chromatography eluting with hexane/EA (50-75%) to afford 630 mg of the title compound. MS (ES⁺): m/z=310 (M+H)⁺

Preparation 2

5-Fluoro-2-nitro-pyridine

To sulfuric acid (46 mL) at 0° C. add 25% hydrogen peroxide (26.98 mL) in the open air. After 5 min add a cold Prepare the following essentially as described for 5-fluoro-2-nitro-pyridine using the corresponding amine:

| Preparation | Compound | MS (ES+): m/z (M + H)+ |
|---|---|---|
| 3 | 3-Bromo-2-methyl-6-nitro-pyridine | 218 |

Preparation 4

1-Isopropyl-4-(2-methyl-6-nitro-pyridin-3-yl)-piperazine

Stir 3-bromo-2-methyl-6-nitro-pyridine (2.46 g), 1-isopropyl-piperazine (2.74 g), tetra-n-butyl ammonium iodide (418.69 mg) and potassium carbonate (1.72 g) in dimethyl sulfoxide (DMSO, 20 mL) at 65° C. overnight. Add EA and water, separate the phases and dry the organic layer over magnesium sulfate and remove the solvent under vacuum. Purify by strong cation exchange cartridge eluting with methanol and then methanol-NH₃ 2 N to afford 2.58 g of the title compound. MS (ES⁺): m/z=265 (M+H)⁺

Prepare the following intermediates essentially as described for 1-isopropyl-4-(2-methyl-6-nitro-pyridin-3-yl)-piperazine using the corresponding bromo derivative:

| Preparation | Compound | MS (ES+): m/z (M + H)+ |
|---|---|---|
| 5 | (2'-Methyl-6'-nitro-3,4,5,6-tetrahydro-2H-[1,3']bipyridinyl-4-yl)-carbamic acid tert-butyl ester | 337 |
| 6 | (6'-Nitro-3,4,5,6-tetrahydro-2H-[1,3']bipyridinyl-4-yl)-carbamic acid tert-butyl ester | 323 |

Preparation 7

5-(4-Isopropyl-piperazin-1-yl)-6-methyl-pyridin-2-ylamine

Stir 1-isopropyl-4-(2-methyl-6-nitro-pyridin-3-yl)-piperazine (2.52 g) and palladium over carbon 10% (600 mg) in methanol (38 mL) and EA (38 mL) under H$_2$ (balloon) overnight. Filter over a celite pad and remove the solvent under vacuum. Purify by silica gel column chromatography eluting with DCM/methanol (0-10%) to afford 2.23 g of the title compound. MS (ES$^+$): m/z=143 (M+H)$^+$.

Prepare the following intermediates essentially as described for 5-(4-isopropyl-piperazin-1-yl)-6-methyl-pyridin-2-ylamine using the corresponding nitro derivative:

| Preparation | Compound | MS (ES+): m/z (M + H)+ |
|---|---|---|
| 8 | (6'-Amino-2'-methyl-3,4,5,6-tetrahydro-2H-[1,3']bipyridinyl-4-yl)-carbamic acid tert-butyl ester | 307 |
| 9 | (6'-Amino-3,4,5,6-tetrahydro-2H-[1,3']bipyridinyl-4-yl)-carbamic acid tert-butyl ester | 293 |

Preparation 10

4-(6-Nitro-pyridin-3-yloxy)-piperidine-1-carboxylic acid tert-butyl ester

Add potassium tert-butoxide (4.84 g) to a solution of tert-butyl 4-hydroxy-1-piperidine-carboxylate (8.76 g) in dimethylacetamide (DMA, 39 mL) at 0° C. under nitrogen. Stir for 1 h and add drop wise a solution 5-fluoro-2-nitro-pyridine (5 g) in DMA (78 mL). Let the reaction stir at RT overnight. Add water and stand for 1 h. Filter, wash with water. Purify by silica gel column chromatography eluting with DCM/EA (0-15%) to afford 5.65 g of the title compound. MS (ES$^+$): m/z=324 (M+H)$^+$.

Preparation 11

4-(6-Amino-pyridin-3-yloxy)-piperidine-1-carboxylic acid tert-butyl ester

Add palladium over carbon 10% (0.6 g) to a suspension of 4-(6-nitro-pyridin-3-yloxy)-piperidine-1-carboxylic acid tert-butyl ester (5.65 g) in a mixture tetrahydrofuran (THF)/methanol (30/30 mL/mL). Hydrogenate in a Parr apparatus at 2 atm overnight. Filter through a celite pad, wash with DCM and methanol. Purify by silica gel column chromatography eluting with DCM/methanol (10%)/ammonia (1%) to afford 5 g of the title compound. MS (ES$^+$): m/z=294 (M+H)$^+$.

Preparation 12

6-Amino-2-methyl-3',6'-dihydro-2'H-[3,4']bipyridinyl-1'-carboxylic acid tert-butyl ester

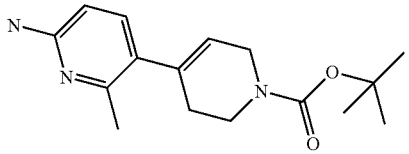

Bubble nitrogen into a mixture of 4-(4,4,5,5-tetramethyl-[1,3,2]dioxaborolan-2-yl)-3,6-dihydro-2H-pyridine-1-carboxylic acid tert-butyl ester (2.46 g) and 5-bromo-6-methyl-pyridin-2-ylamine (1.49 g) in 1,4-dioxane (31.82 mL) for 5 min, then add potassium phosphate tribasic N-hydrate (5.07 g), palladium acetate (35.72 mg), dicyclohexyl-(2',6'-dimethoxy-biphenyl-2-yl)-phosphane (134.69 mg]), water (7.96 mL) and stir at 90° C. for 3 h. Dilute with DCM and wash with water. Dry over sodium sulfate and remove the solvent under vacuum. Purify by silica gel column chromatography eluting with DCM/ethanol 5%/NH$_3$ 0.1%, followed by strong cation exchange cartridge (SCX) eluting with methanol and then methanol-NH$_3$ 2 M to afford 2.12 g of the title compound. MS (ES$^+$): m/z=292 (M+H)$^+$.

Preparation 13

6-Amino-2-methyl-3',4',5',6'-tetrahydro-2'H-[3,4']bipyridinyl-1'-carboxylic acid tert-butyl ester Stir a mixture of 6-amino-2-methyl-3',6'-dihydro-2'H-[3,4']bipyridinyl-1'-carboxylic acid tert-butyl ester (2.12 g) and palladium on carbon 10% wet (330 mg) in methanol (29.30 mL) under H$_2$ (45 psi) for 48 h. Filtered over a celite pad and remove the solvent under vacuum to afford 2.07 g of the title compound. MS (ES$^+$): m/z=292 (M+H)$^+$.

Preparation 14

6-nitro-3',6'-dihydro-2'H-[3,4]bipyridinyl-1'-carboxylic acid tert-butyl ester

Bubble nitrogen into a mixture of 4-(4,4,5,5-tetramethyl-[1,3,2]dioxaborolan-2-yl)-3,6-dihydro-2H-pyridine-1-carboxylic acid tert-butyl ester (19.6 g), 5-bromo-2-nitropyridine (12.87 g), sodium carbonate 2M in water (63.39 mL) and bis(triphenylphosphine)palladium(II) chloride (4.45 g) in 1,4-dioxane (316.94 mL) for 5 min and stir at 80° C. for 5 h. Dilute with DCM and wash with water. Dry over magnesium sulfate and remove the solvent under vacuum. Purify by silica gel chromatography eluting with DCM/EA (0-40%) to afford 8.72 g of the title compound. MS (ES$^+$): m/z=306 (M+H)$^+$.

Preparation 15

6-Amino-3',4',5',6'-tetrahydro-2'H-[3,4]bipyridinyl-1'-carboxylic acid tert-butyl ester Dissolve 6-nitro-3',6'-dihydro-2'H-[3,4]bipyridinyl-1'-carboxylic acid tert-butyl ester (1.89 g) in ethanol (123.80 mL). Hydrogenate with palladium on carbon (H-Cube instrument, 70 bar, 50° C., 1 mL/min) to afford 1.72 g of the title compound. MS (ES$^+$): m/z=278 (M+H)$^+$.

Preparation 16

4-(6-Amino-pyridin-3-ylmethyl)-piperidine-1-carboxylic acid tert-butyl ester Stir for 5 min 4-methylene-piperidine-1-carboxylic acid tert-butyl ester (5.10 g) under nitrogen and add a 0.5 M THF solution of 9-borabicyclo[3.3.1]nonane (77.49 mL). Stir at 75° C. under nitrogen for 1 h. Cool and add 2-amino-5-bromopyridine (3.8 g), potassium carbonate (3.87 g), and 1,1'-biss(diphenylphosphino)ferrocene)palladium(II) chloride (538.10 mg) and a degassed mixture of DMF (47.83 mL) and water (4.78 mL). Stir at 60° C. during 4 h, then at RT over the weekend. Add water and EA. Separate and extract aqueous layer with EA. Combine the organic layers and dry over sodium sulfate and remove the solvent under vacuum. Purify by silica gel column chromatography, eluting with DCM/methanol (1%)/ammonia (0.1%) to DCM/methanol (3%)/ammonia (0.3%). Triturate the residue with EA to afford 1.85 g of the title compound. MS (ES$^+$): m/z=292 (M+H)$^+$.

Prepare the following essentially as described for 4-(6-amino-pyridin-3-ylmethyl)-piperidine-1-carboxylic acid tert-butyl ester using the corresponding bromo derivative:

| Preparation | Compound | MS (ES+): m/z (M + H)+ |
|---|---|---|
| 17 | 4-(6-Amino-2-methyl-pyridin-3-ylmethyl)-piperidine-1-carboxylic acid tert-butyl ester | 306 |

Preparation 18

1-(6-Bromo-pyridin-3-ylmethyl)-4-ethyl-piperazine

Add neat 1-ethylpiperazine (221.44 mL) to a mixture of 6-bromo-pyridine-3-carbaldehyde (300 g) and DCM (5000 mL). Then, add sodium triacetoxyborohydride (372.09 g) in portions and stir at RT for 12 h. Add DCM (1000 mL) and aqueous solution of sodium hydroxide 2 N (1500 mL). Separate the layers and extract twice the aqueous layer with DCM (600 mL). Combine the organic layers and remove the solvent under vacuum, add EA and evaporate to afford 451.3 g of the title compound. MS (ES$^+$): m/z=285 (M+H)$^+$.

Prepare the following essentially as described for 1-(6-bromo-pyridin-3-ylmethyl)-4-ethyl-piperazine using the corresponding amine:

| Preparation | Compound | MS (ES+): m/z (M + H)+ |
|---|---|---|
| 19 | 4-(6-Bromo-pyridin-3-ylmethyl)-piperazine-1-carboxylic acid tert-butyl ester | 357 |

Preparation 20

5-(4-Ethyl-piperazin-1-ylmethyl)-pyridin-2-ylamine

Add lithium 1,1,1,3,3,3-hexamethyl-disilazane (1055 mL) slowly to a degassed mixture of 1-(6-bromo-pyridin-3-ylmethyl)-4-ethyl-piperazine (250 g), dicyclohexylphosphino)biphenyl (18.50 g), tris(dibenzylideneacetone)dipalladium (24.17 g) and THF (250 mL) at 50° C. Heat the mixture at 65° C. overnight. Cool to 37° C. and add water (500 mL). Remove half of the solvent under vacuum and add DCM (2.5 L). Filter over a celite pad and remove part of the solvent. Add methanol (300 mL) and methyl tert-butyl ether (MtBE, 600 mL) to the mixture and cool in an ice bath. Then, add hydrochloric acid 2 M in ethyl ether (800 mL) and a 32% aqueous solution of hydrochloric acid (100 mL). Remove the organic layer, and add an aqueous solution of sodium hydroxide 2 M (2500 mL). Extract the aqueous phase three times with DCM and remove the solvent under vacuum. Solve in 90 mL of toluene at 50° C. until complete dissolution and then add 80 mL of MtBE. Stir overnight at RT. Add additional MtBE (100 mL) for complete precipitation. Filter the solid and dry to afford 108.24 g of the title compound. MS (ES$^+$): m/z=221 (M+H)$^+$.

Prepare the following essentially as described for 5-(4-ethyl-piperazin-1-ylmethyl)-pyridin-2-ylamine using the corresponding 2-bromo-pyridine derivative:

| Preparation | Compound | MS (ES+): m/z (M + H)+ |
|---|---|---|
| 21 | 4-(6-Amino-pyridin-3-ylmethyl)-piperazine-1-carboxylic acid tert-butyl ester | 293 |

Preparation 22

2,4-Dibromo-1-nitro-benzene

Add drop wise fuming nitric acid (101.40 mL) to a solution of 1,3-dibromo benzene (102.51 mL) in concentrated sulfuric acid (322.79 mL) and water (62.39 mL) at 0° C. Warm to RT and stir for 12 h. Pour the reaction on ice-water (1500 mL). Filter the resulting yellow solid under vacuum and dry to afford 178.46 g of the title compound. MS (ES$^+$): m/z=281 (M+H)$^+$.

Preparation 23

(5-Bromo-2-nitro-phenyl)-cyclopentyl-amine

Add cyclopentanamine (32 mL) to a solution of 2,4-dibromo-1-nitro-benzene (20 g) in 1-butanol (160 mL). Heat the mixture at 100° C. overnight. Remove the solvent under vacuum, add water and extract with EA. Wash the organic layer sequentially with an aqueous saturated solution of sodium bicarbonate and then water. Dry over magnesium sulfate and remove the solvent under vacuum to afford 22 g of the title compound. MS (ES$^+$): m/z=286 (M+H)$^+$.

Preparation 24

4-Bromo-N2-cyclopentyl-benzene-1,2-diamine

Add sodium dithionite (107.47 g) to a solution of 5-bromo-2-nitro-phenyl)-cyclopentyl-amine (22 g), THF (150 mL), water (150 mL) and ammonium hydroxide (30 mL). Stir the mixture at RT overnight. Extract twice with EA, dry over magnesium sulfate and remove the solvent under vacuum to afford 14.80 g of the title compound. MS (ES+): m/z=256 (M+H)+.

Preparation 25

6-Bromo-1-cyclopentyl-2-methyl-1H-benzoimidazole

Heat a mixture of 4-bromo-N2-cyclopentyl-benzene-1,2-diamine (10.6 g), triethyl orthoacetate (9.5 ml) and acetic acid (6.3 mL) at 100° C. for 2.5 h. Dilute with DCM and pour onto an aqueous saturated solution of sodium bicarbonate. Dry over sodium sulfate and remove the solvent under vacuum. Purify by silica gel column chromatography, eluting with DCM/ethanol-10% $NH_3$ (0-3%) to afford 10.67 g of the title compound. MS (ES+): m/z=280 (M+H)+.

Preparation 26

N-Isopropyl-acetamide

Add TEA (23.58 mL) to a solution of 2-propanamine (10 g) in DCM (100 mL) at 0° C. Then, carefully add drop wise acetic acid anhydride (16.15 mL). Stir at RT overnight. Remove the solvent under vacuum, dilute with ethyl ether (ether) and filter the solid. Remove the solvent under vacuum. Dilute the oil with ether, add potassium carbonate and stir overnight at RT. Filter the solid and remove the solvent under vacuum to afford 15.62 g of the title compound. NMR (CDCl3) 4.06 (m, 1H), 1.94 (s, 3H), 1.14 (d, 6H).

Prepare the following amides essentially as described for N-isopropyl-acetamide using the corresponding amine:

| Preparation | Compound |
|---|---|
| 27 | N-Cyclopropyl-acetamide |
| 28 | N-Cyclopropylmethyl-acetamide |
| 29 | N-Cyclopentyl-acetamide |

Preparation 30

N-(4-Bromo-2,6-difluoro-phenyl)-N'-isopropyl-acetamidine

Add TEA (10.05 mL) to a mixture of 4-bromo-2,6-difluoro-phenylamine (10.0 g), N-isopropyl acetamide (9.73 g), phosphoryl chloride (6.70 mL) in toluene (150 mL). Heat the mixture to reflux for 3 h. Cool the mixture and remove the solvent under vacuum. Dissolve the crude in DCM, wash with an aqueous saturated solution of sodium bicarbonate several times to remove all traces of acid. Dry over sodium sulfate and remove the solvent under vacuum to afford 14 g of the title compound. MS (ES+): m/z=292 (M+H)+.

Prepare the following intermediates essentially as described for N-(4-bromo-2,6-difluoro-phenyl)-N'-isopropyl-acetamidine using the corresponding acetamide:

| Preparation | Compound | MS (ES+): m/z (M + H)+ |
|---|---|---|
| 31 | N-(4-Bromo-2,6-difluoro-phenyl)-N'-cyclopropyl-acetamidine | 290 |
| 32 | N-(4-Bromo-2,6-difluoro-phenyl)-N'-cyclopropylmethyl-acetamidine | 304 |
| 33 | N-(4-Bromo-2,6-difluoro-phenyl)-N'-cyclopentyl-acetamidine | 318 |

Preparation 34

6-Bromo-4-fluoro-1-isopropyl-2-methyl-1H-benzoimidazole

Add potassium tert-butoxide (811.43 mg) to a solution of N-(4-bromo-2,6-difluoro-phenyl)-N'-isopropyl-acetamidine (2 g) in N-methyl formamide (20 mL). Heat the mixture at 100° C. for 2 h. Cool to RT, add DCM (150 mL), wash three times with saturated sodium chloride aqueous (brine, 300 mL), dry over magnesium sulfate and remove the solvent under vacuum. Add hexane and shake over ultrasound for a few minutes. Filter the solid, repeat addition of hexane/filtration twice to afford 1.86 g of the title compound. MS (ES+): m/z=272 (M+H)+.

Prepare the following intermediates essentially as described for 6-bromo-4-fluoro-1-isopropyl-2-methyl-1H-benzoimidazole using the corresponding acetamidine:

| Preparation | Compound | MS (ES+): m/z (M + H)+ |
|---|---|---|
| 35 | 6-Bromo-1-cyclopropyl-4-fluoro-2-methyl-1H-benzoimidazole | 270 |
| 36 | 6-Bromo-1-cyclopropylmethyl-4-fluoro-2-methyl-1H-benzoimidazole | 284 |
| 37 | 6-Bromo-1-cyclopentyl-4-fluoro-2-methyl-1H-benzoimidazole | 298 |

Preparation 38

4-Fluoro-1-isopropyl-2-methyl-6-(4,4,5,5-tetramethyl-[1,3,2]dioxaborolan-2-yl)-1H-benzoimidazole Bubble nitrogen into a mixture of 6-bromo-4-fluoro-1-isopropyl-2-methyl-1H-benzoimidazole (30.0 g), bis(pinacolato)diboron (42.15 g), tricyclohexylphosphine (5.43 g), potassium acetate (32.58 g), and DMSO (200 mL). Add palladium acetate (2.8 g) and heat in pre-heated oil bath at 90° C. for 1 h. Dilute with EA (200 mL) and filter over a celite pad. Wash the mixture with brine (100 mL), dry over sodium sulfate and remove the solvent under vacuum. Triturate with hexane and filter the solid to afford 27 g of the title compound. MS (ES+): m/z=319 (M+H)+.

Prepare the following intermediates essentially as described for 4-fluoro-1-isopropyl-2-methyl-6-(4,4,5,5-tetramethyl-[1,3,2]dioxaborolan-2-yl)-1H-benzoimidazole using the corresponding 6-bromo-benzoimidazole derivatives:

| Preparation | Compound | MS (ES+): m/z (M + H)+ |
|---|---|---|
| 39 | 1-Cyclopropyl-4-fluoro-2-methyl-6-(4,4,5,5-tetramethyl-[1,3,2]dioxaborolan-2-yl)-1H-benzoimidazole | 317 |
| 40 | 1-Cyclopentyl-2-methyl-6-(4,4,5,5-tetramethyl-[1,3,2]dioxaborolan-2-yl)-1H-benzoimidazole | 327 |
| 41 | 1-Cyclopropylmethyl-4-fluoro-2-methyl-6-(4,4,5,5-tetramethyl-[1,3,2]dioxaborolan-2-yl)-1H-benzoimidazole | 331 |
| 42 | 1-Cyclopentyl-4-fluoro-2-methyl-6-(4,4,5,5-tetramethyl-[1,3,2]dioxaborolan-2-yl)-1H-benzoimidazole | 345 |

Preparation 43

6-(2-Chloro-5-fluoro-pyrimidin-4-yl)-4-fluoro-1-isopropyl-2-methyl-1H-benzoimidazole Bubble nitrogen into a mixture of 2,4-dichloro-5-fluoro-pyrimidine (12.7 g), bis(triphenylphosphine)palladium(II) chloride (4.9 g), sodium carbonate 2 M in water (103.7 mL) and 1,2-dimethoxyethane (120 mL). Heat in a pre-heated oil bath at 80° C. and add drop wise a solution of 4-fluoro-1-isopropyl-2-methyl-6-(4,4,5,5-tetramethyl-[1,3,2]dioxaborolan-2-yl)-1H-benzoimidazole (22 g) in 1,2-dimethoxyethane (200 mL). Stir the mixture at 84° C. for 1 h. Cool to RT, add EA (800 mL) and wash twice with brine (100 mL). Dry over magnesium sulfate and remove the solvent under vacuum. Triturate with acetonitrile to afford 14.4 g of the title compound. MS (ES+): m/z=323 (M+H)+.

Prepare the following intermediates essentially as described for 6-(2-chloro-5-fluoro-pyrimidin-4-yl)-4-fluoro-1-isopropyl-2-methyl-1H-benzoimidazole using the corresponding dichloro-pyrimidine and boronate derivatives:

| Preparation | Compound | MS (ES+): m/z (M + H)+ |
|---|---|---|
| 44 | 6-(2-Chloro-5-fluoro-pyrimidin-4-yl)-1-cyclopropyl-4-fluoro-2-methyl-1H-benzoimidazole | 321 |
| 45 | 6-(2-Chloro-5-fluoro-pyrimidin-4-yl)-1-cyclopentyl-2-methyl-1H-benzoimidazole | 331 |
| 46 | 6-(2-Chloro-5-fluoro-pyrimidin-4-yl)-1-cyclopropylmethyl-4-fluoro-2-methyl-1H-benzoimidazole | 335 |
| 47 | 6-(2-Chloro-pyrimidin-4-yl)-1-cyclopentyl-4-fluoro-2-methyl-1H-benzoimidazole | 331 |
| 48 | 6-(2-Chloro-pyrimidin-4-yl)-4-fluoro-1-isopropyl-2-methyl-1H-benzoimidazole | 305 |

Prepare the following intermediates essentially as described for [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine below using the corresponding amine and chloro-pyrimidine derivatives:

| Preparation | Compound | MS (ES+): m/z (M + H)+ |
|---|---|---|
| 49 | 4-{6-[5-Fluoro-4-(7-fluoro-3-isopropyl-2-methyl-3H-benzoimidazol-5-yl)-pyrimidin-2-ylamino]-pyridin-3-ylmethyl}-piperazine-1-carboxylic acid tert-butyl ester | 579 |
| 50 | 4-{6-[4-(3-Cyclopropyl-7-fluoro-2-methyl-3H-benzoimidazol-5-yl)-5-fluoro-pyrimidin-2-ylamino]-pyridin-3-ylmethyl}-piperidine-1-carboxylic acid tert-butyl ester | 576 |
| 51 | 4-{6-[5-Fluoro-4-(7-fluoro-3-isopropyl-2-methyl-3H-benzoimidazol-5-yl)-pyrimidin-2-ylamino]-2-methyl-pyridin-3-ylmethyl}-piperidine-1-carboxylic acid tert-butyl ester | 592 |
| 52 | 6-[4-(3-Cyclopentyl-2-methyl-3H-benzoimidazol-5-yl)-5-fluoro-pyrimidin-2-ylamino]-3',4',5',6'-tetrahydro-2'H-[3,4']bipyridinyl-1'-carboxylic acid tert-butyl ester | 572 |
| 53 | 6-[5-Fluoro-4-(7-fluoro-3-isopropyl-2-methyl-3H-benzoimidazol-5-yl)-pyrimidin-2-ylamino]-2-methyl-3',4',5',6'-tetrahydro-2'H-[3,4']bipyridinyl-1'-carboxylic acid tert-butyl ester | 578 |
| 54 | 4-{6-[5-Fluoro-4-(7-fluoro-3-isopropyl-2-methyl-3H-benzoimidazol-5-yl)-pyrimidin-2-ylamino]-pyridin-3-yloxy}-piperidine-1-carboxylic acid tert-butyl ester | 580 |
| 55 | {6'-[5-Fluoro-4-(7-fluoro-3-isopropyl-2-methyl-3H-benzoimidazol-5-yl)-pyrimidin-2-ylamino]-2'-methyl-3,4,5,6-tetrahydro-2H-[1,3']bipyridinyl-4-yl}-carbamic acid tert-butyl ester | 593 |
| 56 | {6'-[4-(3-Cyclopentyl-7-fluoro-2-methyl-3H-benzoimidazol-5-yl)-pyrimidin-2-ylamino]-3,4,5,6-tetrahydro-2H-[1,3']bipyridinyl-4-yl}-carbamic acid tert-butyl ester | 587 |
| 57 | 4-{6-[4-(7-Fluoro-3-isopropyl-2-methyl-3H-benzoimidazol-5-yl)-pyrimidin-2-ylamino]-pyridin-3-ylsulfanyl}-piperidine-1-carboxylic acid tert-butyl ester | 578 |

Preparation 58

[5-Fluoro-4-(7-fluoro-3-isopropyl-2-methyl-3H-benzoimidazol-5-yl)-pyrimidin-2-yl]-(5-piperazin-1-ylmethyl-pyridin-2-yl)-amine

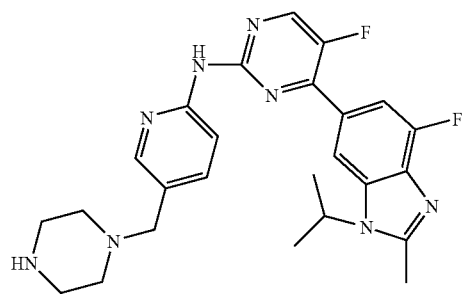

To a mixture of 4-{6-[5-fluoro-4-(7-fluoro-3-isopropyl-2-methyl-3H-benzoimidazol-5-yl)-pyrimidin-2-ylamino]-pyridin-3-ylmethyl}-piperazine-1-carboxylic acid tert-butyl ester (150 mg) in DCM (10 mL) and methanol (10 mL) add hydrogen chloride 4M in dioxane (194 μL). Stir 10 min and remove the solvent under vacuum. Purify by strong cation exchange cartridge (SCX) eluting with methanol and then methanol-NH$_3$ 2M followed by silica gel column chromatography eluting with DCM/methanol-NH$_3$ 2M (3%) to afford 120 mg of the title compound. MS (ES+): m/z=479 (M+H)+.

Prepare the following intermediates essentially as described for [5-fluoro-4-(7-fluoro-3-isopropyl-2-methyl-3H-benzoimidazol-5-yl)-pyrimidin-2-yl]-(5-piperazin-1-yl-methyl-pyridin-2-yl)-amine:

| Preparation | Structure | Compound Name | MS (ES+): m/z (M + H)+ |
|---|---|---|---|
| 59 | 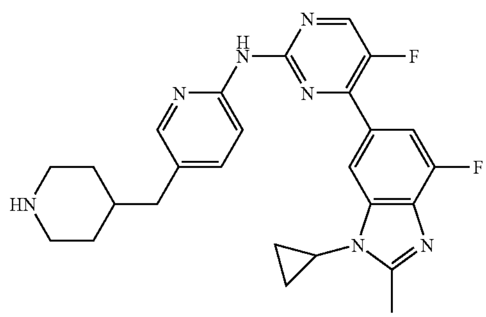 | [4-(3-Cyclopropyl-7-fluoro-2-methyl-3H-benzoimidazol-5-yl)-5-fluoro-pyrimidin-2-yl]-[5-piperidin-4-ylmethyl-pyridin-2-yl)-amine | 476 |
| 60 | 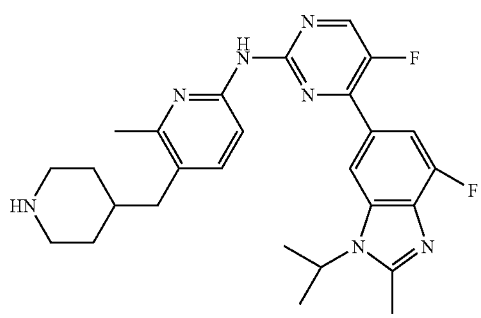 | [5-Fluoro-4-(7-fluoro-3-isopropyl-2-methyl-3H-benzoimidazol-5-yl)-pyrimidin-2-yl]-(6-methyl-5-piperidin-4-ylmethyl-pyridin-piperidin-4-ylmethyl-pyridin-2-yl)amine | 492 |
| 61 | 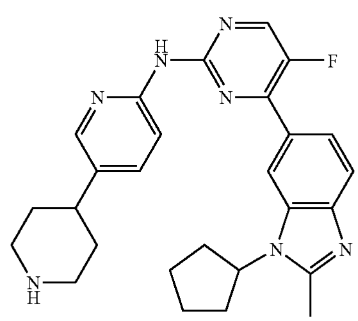 | [4-(3-Cyclopentyl-2-methyl-3H-benzoimidazol-5-yl)-5-fluoro-pyrimidin-2-yl]-(1',2',3',4',5',6'-hexahydro-[3,4']bipyridinyl-6-yl)-amine | 472 |
| 62 | 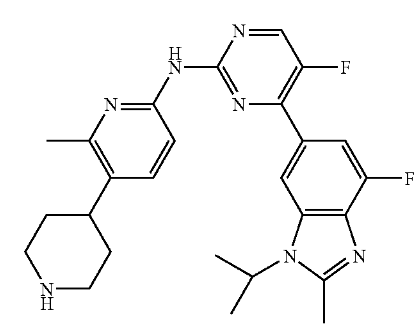 | [5-Fluoro-4-(7-fluoro-3-isopropyl-2-methyl-3H-benzoimidazol-5-yl)-pyrimidin-2-yl]-(2-methyl-1',2',3',4',5',6'-hexahydro-[3,4']bipyridinyl-6-yl)-amine | 478 |

-continued

| Preparation | Structure | Compound Name | MS (ES+): m/z (M + H)+ |
|---|---|---|---|
| 63 | 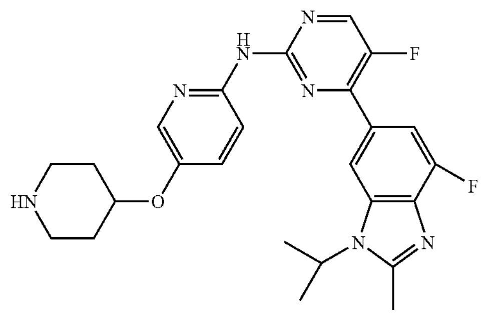 | [5-Fluoro-4-(7-fluoro-3-isopropyl-2-methyl-3H-benzoimidazol-5-yl)-pyrimidin-2-yl]-[5-(piperidin-4-yloxy)-pyridin-2-yl]-amine | 480 |
| 64 | 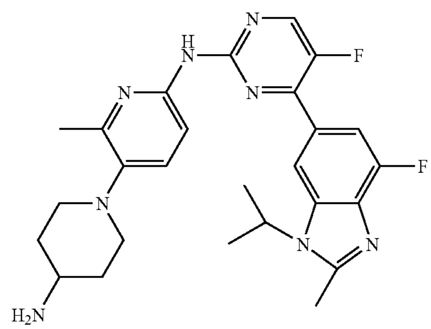 | N6'-[5-Fluoro-4-(7-fluoro-3-isopropyl-2-methyl-3H-benzoimidazol-5-yl)-pyrimidin-2-yl]-2'-methyl-3,4,5,6-tetrahydro-2H-[1,3']bipyridinyl-4,6'-diamine | 493 |
| 65 | 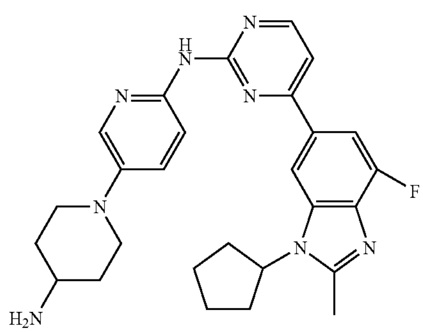 | N6'-[4-(3-Cyclopentyl-7-fluoro-2-methyl-3H-benzoimidazol-5-yl)-pyrimidin-2-yl]-3,4,5,6-tetrahydro-2H-[1,3']bipyridinyl-4,6'-diamine | 487 |
| 66 | 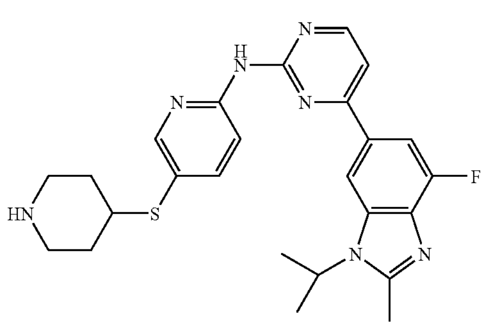 | [4-(7-Fluoro-3-isopropyl-2-methyl-3H-benzoimidazol-5-yl)-pyrimidin-2-yl]-[5-(piperidin-4-ylsulfanyl)-pyridin-2-yl]-amine | 478 |

Example 1

[5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine

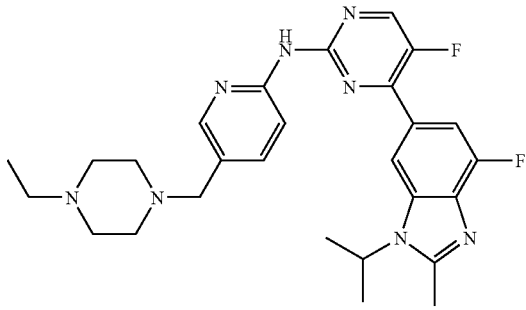

Bubble nitrogen into a mixture of 6-(2-chloro-5-fluoro-pyrimidin-4-yl)-4-fluoro-1-isopropyl-2-methyl-1H-benzoimidazole (15.9 g), 5-(4-ethyl-piperazin-1-ylmethyl)-pyridin-2-ylamine (10.85 g), cesium carbonate (32.10 g), tris(dibenzylideneacetone) dipalladium (1.82 g), 4,5-bis(diphenylphosphino)-9,9-dimethylxanthene (2.35 g) in 1,4-dioxane (197.06 mL). Heat the mixture in a pre-heated oil bath at 110° C. for 2 h. Cool to RT, dilute with DCM and filter over a celite pad. Remove the solvent under vacuum and purify by silica gel column chromatography, eluting with DCM/methanol (2%) and then DCM/methanol-$NH_3$ 2 M 2% to afford 22.11 g of the title compound. MS (ES$^+$): m/z=507 (M+H)$^+$.

Prepare the following examples essentially as described for [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine using the corresponding amine and chloro-pyrimidine derivatives:

| Example | Structure | Compound Name | MS (ES+): m/z (M + H)+ |
|---|---|---|---|
| 2 | 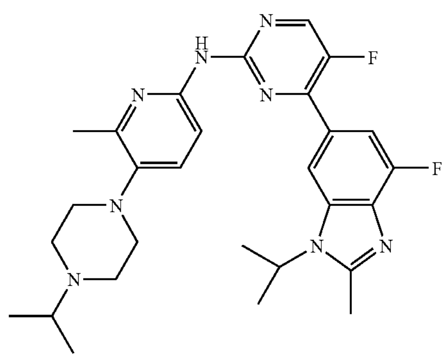 | [5-Fluoro-4-(7-fluoro-3-isopropyl-2-methyl-3H-benzoimidazol-5-yl)-pyrimidin-2-yl]-[5-(4-isopropyl-piperazin-1-yl)-6-methyl-pyridin-2-yl]-amine | 521 |
| 3 | 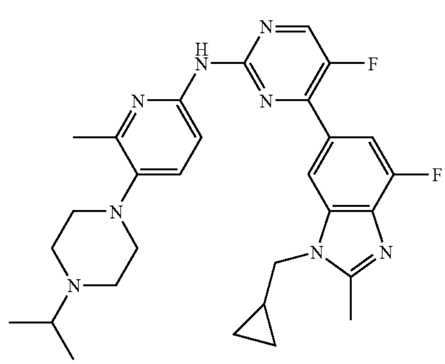 | [4-(3-Cyclopropylmethyl-7-fluoro-2-methyl-3H-benzoimidazol-5-yl)-5-fluoro-pyrimidin-2-yl]-[5-(4-isopropyl-piperazin-1-yl)-6-methyl-pyridin-2-yl]-amine | 533 |

Example 4

[5-Fluoro-4-(7-fluoro-3-isopropyl-2-methyl-3H-benzoimidazol-5-yl)-pyrimidin-2-yl]-[5-(4-isopropyl-piperazin-1-ylmethyl)-pyridin-2-yl]-amine

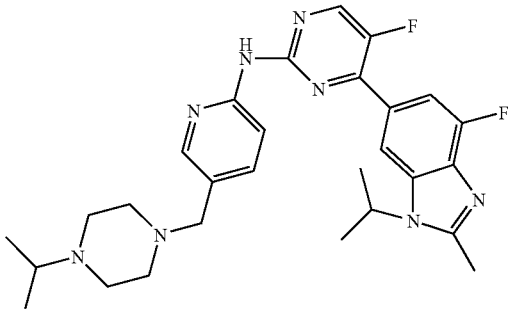

Add sodium triacetoxyborohydride (299.9 mg) to a mixture of [5-fluoro-4-(7-fluoro-3-isopropyl-2-methyl-3H-benzoimidazol-5-yl)-pyrimidin-2-yl]-(5-piperazin-1-ylmethyl-pyridin-2-yl)-amine (130 mg), acetone (31.6 µL), 1,2-dichloroethane (9 mL) and acetic acid (16.3 µL). Heat at 60° C. for 1 h. Remove the solvent under vacuum. Purify by strong cation exchange cartridge (SCX) eluting with methanol and then methanol-NH$_3$ 2 M followed by silica gel column chromatography eluting with DCM/methanol-NH$_3$ 2 M (3%) to afford 115 mg of the title compound. MS (ES$^+$): m/z=521 (M+H)$^+$.

Prepare the following examples essentially as described for [5-fluoro-4-(7-fluoro-3-isopropyl-2-methyl-3H-benzoimidazol-5-yl)-pyrimidin-2-yl]-[5-(4-isopropyl-piperazin-1-ylmethyl)-pyridin-2-yl]-amine using the corresponding amines:

| Example | Structure | Compound Name | MS (ES+): m/z (M + H)+ |
|---|---|---|---|
| 5 | 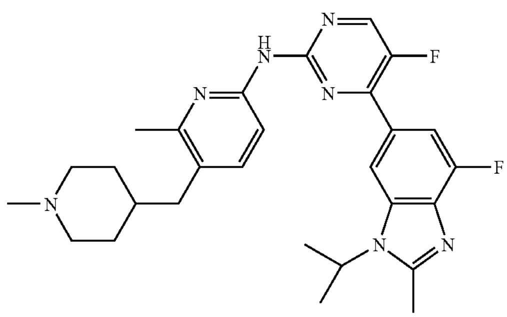 | [5-Fluoro-4-(7-fluoro-3-isopropyl-2-methyl-3H-benzoimidazol-5-yl)-pyrimidin-2-yl]-[6-methyl-5-(1-methyl-piperidin-4-ylmethyl)-pyridin-2-yl]-amine | 506 |
| 6 | 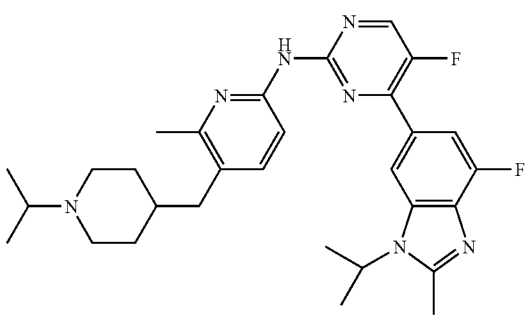 | [5-Fluoro-4-(7-fluoro-3-isopropyl-2-methyl-3H-benzoimidazol-5-yl)-pyrimdiin-2-yl]-[5-(1-isopropyl-piperidin-4-ylmethyl)-6-methyl-pyridin-2-yl]-amine | 534 |
| 7 | 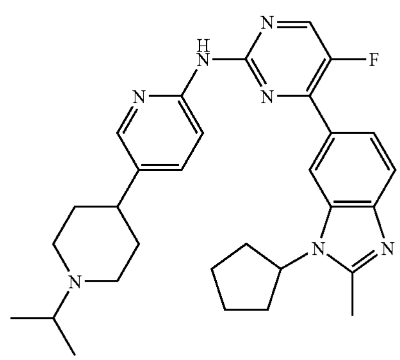 | [4-(3-Cyclopentyl-2-methyl-3H-benzoimidazol-5-yl)-5-fluoro-pyrimidin-2-yl]-[1'-isopropyl-1',2',3',4',5',6'-hexahydro-[3,4']bipyridinyl-6-yl)-amine | 514 |

-continued

| Example | Structure | Compound Name | MS (ES+): m/z (M + H)+ |
|---|---|---|---|
| 8 | 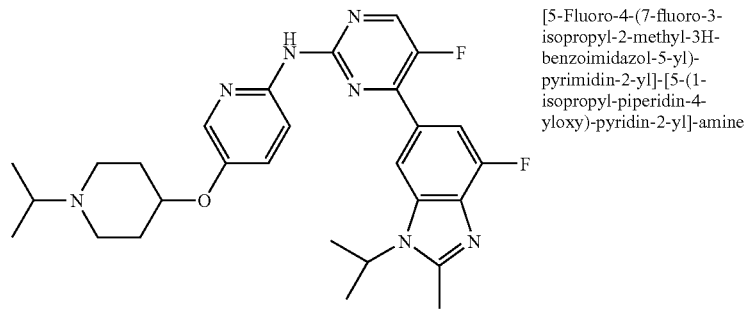 | [5-Fluoro-4-(7-fluoro-3-isopropyl-2-methyl-3H-benzoimidazol-5-yl)-pyrimidin-2-yl]-[5-(1-isopropyl-piperidin-4-yloxy)-pyridin-2-yl]-amine | 522 |

Example 9
[4-(3-Cyclopropyl-7-fluoro-2-methyl-3H-benzoimidazol-5-yl)-5-fluoro-pyrimidin-2-yl]-[5-(1-ethyl-piperidin-4-ylmethyl)-pyridin-2-yl]-amine

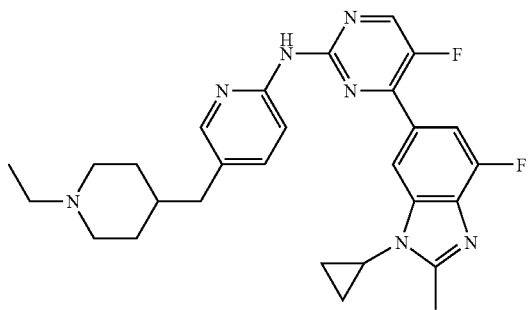

Add sodium triacetoxyborohydride (720 mg) to a mixture of [4-(3-cyclopropyl-7-fluoro-2-methyl-3H-benzoimidazol-5-yl)-5-fluoro-pyrimidin-2-yl]-(5-piperidin-4-ylmethyl-pyridin-2-yl)-amine (110 mg), 1,2 dichloroethane (1.14 mL) and acetic acid (2709 µL). Heat at 60° C. for 1 h. Remove the solvent under vacuum. Purify by strong cation exchange cartridge (SCX) eluting with methanol and then methanol-NH$_3$ 2M followed by silica gel column chromatography eluting with DCM/methanol-NH$_3$ 2M (3%) to afford 80 mg of the title compound. MS (ES$^+$): m/z=504 (M+H)$^+$.

Prepare the following examples essentially as described for [4-(3-cyclopropyl-7-fluoro-2-methyl-3H-benzoimidazol-5-yl)-5-fluoro-pyrimidin-2-yl]-[5-(1-ethyl-piperidin-4-ylmethyl)-pyridin-2-yl]-amine using the corresponding amines.

| Example | Structure | Compound Name | MS (ES+): m/z (M + H)+ |
|---|---|---|---|
| 10 | 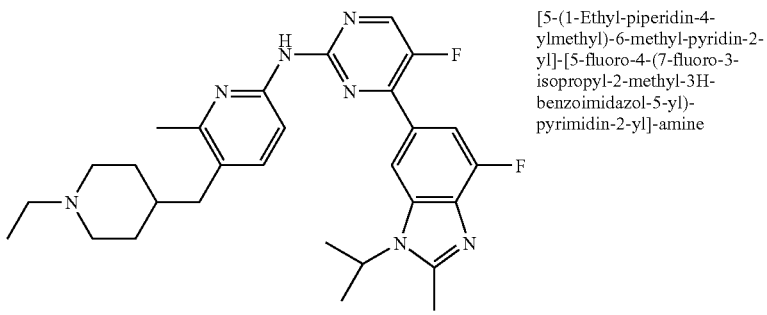 | [5-(1-Ethyl-piperidin-4-ylmethyl)-6-methyl-pyridin-2-yl]-[5-fluoro-4-(7-fluoro-3-isopropyl-2-methyl-3H-benzoimidazol-5-yl)-pyrimidin-2-yl]-amine | 520 |

-continued

| Example | Structure | Compound Name | MS (ES+): m/z (M + H)+ |
|---|---|---|---|
| 11 | 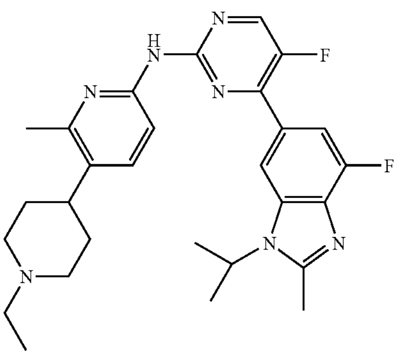 | (1'-Ethyl-2-methyl-1',2',3',4',5',6'-hexahydro-[3,4']bipyridinyl-6-yl)-[5-fluoro-4-(7-fluoro-3-isopropyl-2-methyl-3H-benzoimidazol-5-yl)-pyrimidin-2-yl]-amine | 506 |
| 12 | 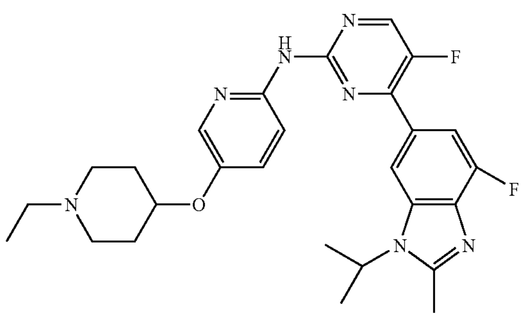 | [5-(1-Ethyl-piperidin-4-yloxy)-pyridin-2-yl]-[5-fluoro-4-(7-fluoro-3-isopropyl-2-methyl-3H-benzoimidazol-5-yl)-pyrimidin-2-yl]-amine | 508 |
| 13 | 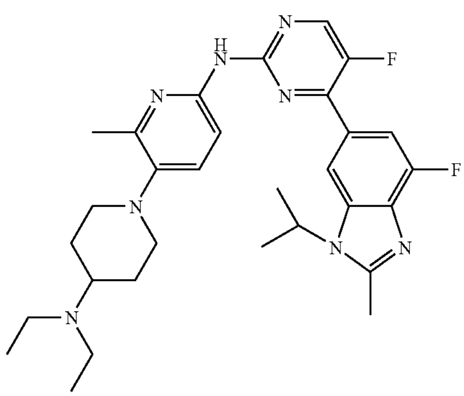 | $N^4,N^4$-Diethyl-N6'-[5-fluoro-4-(7-fluoro-3-isopropyl-2-methyl-3H-benzoimidazol-5-yl)-pyrimidin-2-yl]-2'-methyl-3,4,5,6-tetrahydro-2H-[1,3']bipyridinyl-4,6'-diamine | 549 |
| 14 | 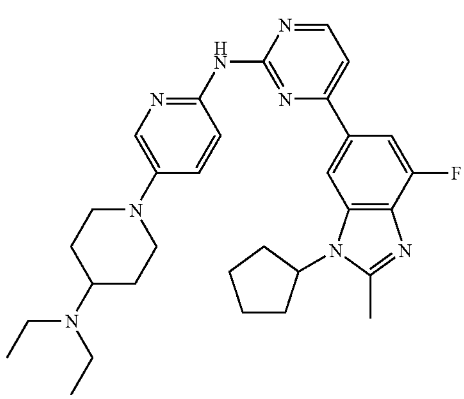 | N6'-[4-(3-Cyclopentyl-7-fluoro-2-methyl-3H-benzoimidazol-5-yl)-pyrimidin-2-yl]-N4,N4-diethyl-3,4,5,6-tetrahydro-2H-[1,3']bipyridinyl-4,6'-diamine | 543 |

| Example | Structure | Compound Name | MS (ES+): m/z (M + H)+ |
|---|---|---|---|
| 15 | 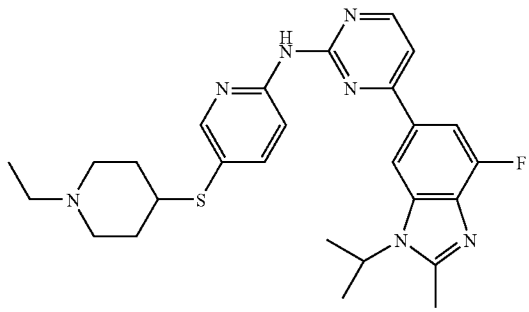 | [5-(1-Ethyl-piperidin-4-ylsulfanyl)-pyridin-2-yl]-[4-(7-fluoro-3-isopropyl-2-methyl-3H-benzoimidazol-5-yl)-pyrimidin-2-yl]-amine | 506 |

Example 16

[5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine methanesulfonate Add methanosulfonic acid (63.59 mL) to a solution of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine (17.3 g) in a mixture of DCM (100 mL) and methanol (100 mL). Stir the solution for 1 h and remove the solvent under vacuum. Triturate with MtBE and filtrate the solid to afford 20.4 g of the title compound. MS (ES+): m/z=507 (M+H)+.

Prepare the following examples essentially as described for [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine methanesulfonate:

| Example | Compound | MS (ES+): m/z (M + H)+ |
|---|---|---|
| 17 | [5-Fluoro-4-(7-fluoro-3-isopropyl-2-methyl-3H-benzoimidazol-5-yl)-pyrimidin-2-yl]-[5-(4-isopropyl-piperazin-1-yl)-6-methyl-pyridin-2-yl]-amine methanesulfonate | 521 |
| 18 | [4-(3-Cyclopropylmethyl-7-fluoro-2-methyl-3H-benzoimidazol-5-yl)-5-fluoro-pyrimidin-2-yl]-[5-(4-isopropyl-piperazin-1-yl)-6-methyl-pyridin-2-yl]-amine methanesulfonate | 533 |
| 19 | [5-Fluoro-4-(7-fluoro-3-isopropyl-2-methyl-3H-benzoimidazol-5-yl)-pyrimidin-2-yl]-[5-(4-isopropyl-piperazin-1-ylmethyl)-pyridin-2-yl]-amine methanesulfonate | 521 |
| 20 | [5-Fluoro-4-(7-fluoro-3-isopropyl-2-methyl-3H-benzoimidazol-5-yl)-pyrimidin-2-yl]-[6-methyl-5-(1-methyl-piperidin-4-ylmethyl)-pyridin-2-yl]-amine methanesulfonate | 506 |
| 21 | [5-Fluoro-4-(7-fluoro-3-isopropyl-2-methyl-3H-benzoimidazol-5-yl)-pyrimidin-2-yl]-[5-(1-isopropyl-piperidin-4-ylmethyl)-6-methyl-pyridin-2-yl]-amine methanesulfonate | 534 |
| 22 | [4-(3-Cyclopentyl-2-methyl-3H-benzoimidazol-5-yl)-5-fluoro-pyrimidin-2-yl]-(1'-isopropyl-1',2',3',4',5',6'-hexahydro-[3,4']bipyridinyl-6-yl)-amine methanesulfonate | 514 |
| 23 | [5-Fluoro-4-(7-fluoro-3-isopropyl-2-methyl-3H-benzoimidazol-5-yl)-pyrimidin-2-yl]-[5-(1-isopropyl-piperidin-4-yloxy)-pyridin-2-yl]-amine methanesulfonate | 522 |
| 24 | [4-(3-Cyclopropyl-7-fluoro-2-methyl-3H-benzoimidazol-5-yl)-5-fluoro-pyrimidin-2-yl]-[5-(1-ethyl-piperidin-4-ylmethyl)-pyridin-2-yl]-amine methanesulfonate | 504 |
| 25 | [5-(1-Ethyl-piperidin-4-ylmethyl)-6-methyl-pyridin-2-yl]-[5-fluoro-4-(7-fluoro-3-isopropyl-2-methyl-3H-benzoimidazol-5-yl)-pyrimidin-2-yl]-amine methanesulfonate | 520 |
| 26 | (1'-Ethyl-2-methyl-1',2',3',4',5',6'-hexahydro-[3,4']bipyridinyl-6-yl)-[5-fluoro-4-(7-fluoro-3-isopropyl-2-methyl-3H-benzoimidazol-5-yl)-pyrimidin-2-yl]-amine methanesulfonate | 506 |
| 27 | [5-(1-Ethyl-piperidin-4-yloxy)-pyridin-2-yl]-[5-fluoro-4-(7-fluoro-3-isopropyl-2-methyl-3H-benzoimidazol-5-yl)-pyrimidin-2-yl]-amine methanesulfonate | 508 |
| 28 | N4,N4-Diethyl-N6'-[5-fluoro-4-(7-fluoro-3-isopropyl-2-methyl-3H-benzoimidazol-5-yl)-pyrimidin-2-yl]-2'-methyl-3,4,5,6-tetrahydro-2H-[1,3']bipyridinyl-4,6'-diamine methanesulfonate | 549 |
| 29 | N6'-[4-(3-Cyclopentyl-7-fluoro-2-methyl-3H-benzoimidazol-5-yl)-pyrimidin-2-yl]-N4,N4-diethyl-3,4,5,6-tetrahydro-2H-[1,3']bipyridinyl-4,6'-diamine methanesulfonate | 543 |
| 30 | [5-(1-Ethyl-piperidin-4-ylsulfanyl)-pyridin-2-yl]-[4-(7-fluoro-3-isopropyl-2-methyl-3H-benzoimidazol-5-yl)-pyrimidin-2-yl]-amine methanesulfonate | 506 |

Example 31

[5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine Crystalline Form I Mix 102.1 mg of amorphous [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine with 2 mL acetone. Isolate the precipitated solid by vacuum filtration, producing a light yellow cake and dry in place on the filtration apparatus for 30 min, giving 72.1 mg of a solid. Place the solid in a 100° C. vacuum oven for 3 h.

Representative XRD peaks of form I are shown in Table 1.

Example 32

[5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine Crystalline Form III Mix 208 mg of amorphous [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine with 4 mL acetone. Slurry the suspension for 2 h at 60° C. while stirring at 1000 rpm, and then isolate the solid by vacuum filtration, producing a light yellow cake. Dry in place on the filtration apparatus for 30 min, giving 112 mg of a solid (54% yield). Place in an 80° C. vacuum oven for 3 h.

Representative XRD peaks of form III are shown in Table 2. The peak positions were verified using an external standard.

X-Ray Powder Diffraction

The XRD patterns of the crystals are obtained on a Bruker D8 Advance X-ray powder diffractometer, equipped with a CuKα source (λ=1.54056 Å) and a Vantec detector, operating at 50 kV and 40 mA. Each sample is scanned between 4 and 40° in 2θ, with a step size of 0.02° in 2θ and a scan rate of 9.0 seconds/step, and with 1 mm divergence and receiving slits and a 0.1 mm detector slit. The dry powder is packed into recessed top-loading sample holder and a smooth surface is obtained using a glass slide. The crystal form diffraction patterns are collected at ambient temperature and relative humidity. The background for the Form III crystal is removed prior to peak picking whereas the background is not removed for Form I.

It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.1 in 2θ will take into account these potential variations without hindering the unequivocal identification of the indicated crystal form.

Confirmation of a crystal form may be made based on any unique combination of distinguishing peaks (in units of ° 2θ), typically the more prominent peaks. Thus, a prepared sample of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine crystalline form I is characterized by an XRD pattern using CuKα radiation as having diffraction peaks (2-theta values) as described in Table 1 below, and in particular having peaks at 4.51 in combination with one or more of the peaks selected from the group consisting of 13.09, 16.31, and 18.82; with a tolerance for the diffraction angles of 0.1 degrees.

Table 1: X-ray powder diffraction peaks of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine crystalline form I.

| Angle ° 2θ | d value Angstrom | Intensity % |
| --- | --- | --- |
| 4.51 | 19.60 | 100 |
| 5.89 | 15.00 | 4 |
| 8.98 | 9.84 | 1.5 |
| 11.20 | 7.89 | 2.3 |
| 12.57 | 7.04 | 1.9 |
| 13.09 | 6.76 | 7 |
| 15.93 | 5.56 | 3 |
| 16.31 | 5.43 | 4.4 |
| 17.01 | 5.21 | 1.9 |
| 18.58 | 4.77 | 3.1 |
| 18.82 | 4.71 | 3.6 |
| 20.86 | 4.26 | 1.5 |
| 21.90 | 4.06 | 2.2 |
| 23.12 | 3.84 | 2.4 |
| 23.53 | 3.78 | 3.7 |
| 26.71 | 3.33 | 2.4 |
| 26.85 | 3.32 | 2 |

A prepared sample of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine crystalline form III is characterized by an XRD pattern using CuKα radiation as having diffraction peaks (2-theta values) as described in the Table 2 below, and in particular having peaks at 21.29 in combination with one or more of the peaks at 11.54, 10.91, and 12.13; with a tolerance for the diffraction angles of 0.1 degrees.

Table 2: X-ray powder diffraction peaks of [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine crystalline form III.

| Angle ° 2θ | d value Angstrom | Intensity % |
| --- | --- | --- |
| 7.44 | 11.87 | 8 |
| 10.91 | 8.11 | 19 |
| 11.54 | 7.66 | 38 |
| 12.13 | 7.29 | 18 |
| 13.89 | 6.37 | 25 |
| 14.91 | 5.94 | 20 |
| 15.63 | 5.67 | 27 |
| 16.06 | 5.52 | 11 |
| 18.59 | 4.77 | 21 |
| 18.94 | 4.68 | 26 |
| 20.43 | 4.34 | 21 |
| 21.29 | 4.17 | 100 |
| 21.91 | 4.05 | 37 |
| 22.13 | 4.01 | 12 |
| 22.45 | 3.96 | 8 |
| 23.12 | 3.84 | 6 |
| 23.42 | 3.80 | 9 |
| 25.95 | 3.43 | 17 |
| 29.42 | 3.03 | 9 |

Solid-State $^{13}$C NMR

Cross polarization/magic angle spinning (CP/MAS) NMR (solid-state NMR or SSNMR) spectra is obtained on a Bruker Avance III 400 wide-bore NMR spectrometer operating at $^1$H and $^{13}C$ frequencies of 400.131 and 100.623 MHz, respectively, and using a Bruker 4 mm double-resonance probe. The MAS rate is set to 5 or 10 kHz using a Bruker MAS-II controller; spinning speeds are maintained within 2 Hz of the set point. SPINAL64 decoupling at a proton nutation frequency of 100 kHz is used for heteronuclear decoupling. Spinning sidebands are eliminated by a five-pulse total sideband suppression (TOSS) sequence. The CP contact time for transferring magnetization from protons to carbons is set to 4 ms and a linear power ramp from 93.5 to 46.9 kHz is used on the $^1H$ channel to enhance CP efficiency. The acquisition time is set to 34 ms and spectra are acquired over a spectral width of 30 kHz with a recycle delay of 5 s. The sample temperature is regulated to 297±1 K in order to minimize frictional heating caused by sample spinning. The $^{13}C$ chemical shifts are externally referenced (±0.05 ppm) to the proton-decoupled $^{13}C$ peak of neat (liquid) tetramethylsilane via the high-field resonance of adamantine ($\delta$=29.5 ppm). A peak list of chemical shifts for [5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine crystalline form III is as follows:

$^{13}C$-NMR: ν(F1) (ppm) 11.7, 12.9, 20.5, 48.6, 52.5, 59.4, 108.9, 110.0, 112.7, 127.3, 129.4, 135.5, 136.4, 148.8, 150.1, 152.2, 154.5, 156.3.

Example 33

[5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine Crystalline Form III Route B

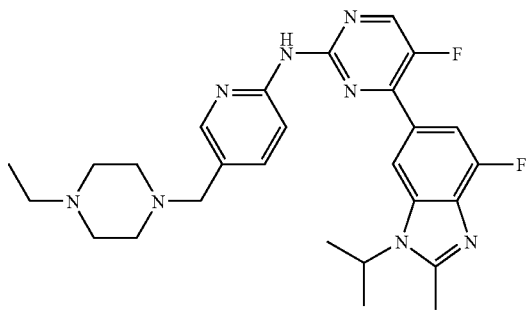

a.
1-(6-Bromo-pyridin-3-ylmethyl)-4-ethyl-piperazine

Add neat 1-ethylpiperazine (5.6 kg) to a mixture of 6-bromo-pyridine-3-carbaldehyde (8.3 kg) and DCM (186 kg). Then, add sodium triacetoxyborohydride (10.9 kg) in portions and stir at 20-30° C. for 12 h. Quench the reaction into a mixture of DCM (36 kg) and aqueous solution of sodium hydroxide 2 N (46 kg). Separate the layers and extract twice the aqueous layer with DCM (24×2 kg). Combine the organic layers, wash with brine (50×2 kg) and remove the solvent under vacuum to afford 11.5 kg of the title compound. MS (ES$^+$): m/z=285 (M+H)$^+$.

b.
5-(4-Ethyl-piperazin-1-ylmethyl)-pyridin-2-ylamine

Add liquid ammonia (50.0 kg) to a degassed mixture of 1-(6-bromo-pyridin-3-ylmethyl)-4-ethyl-piperazine (14.2 kg), cuprous oxide (200 g), and MeOH (57 kg) at T≦40° C. Heat the mixture at 65-75° C. overnight. Cool to 20-30° C. and filter over a Celite® pad. Concentrate the filtrate and add DCM (113 kg) and adjust the pH to 12-14 with sodium hydroxide 2N (23 kg) separate the phases and wash the organic phase with DCM (58×2 kg) and combine the organic layers. Filter the mixture through Celite® and concentrate. Dissolve the residue in toluene (9.7 kg) and crystallize by the addition of MtBE (8.3 kg) to give 6.0 kg of the title compound. Obtain further purification through a toluene recrystallization. MS (ES$^+$): m/z=221 (M+H)$^+$.

c. N-Isopropyl-acetamide

Add potassium carbonate (28 kg) to a solution of 2-propanamine (12 kg) in ethyl acetate (108 kg) at <20° C. Cool the mixture to 5-0° C. and add acetyl chloride (16.7 kg) at about 2-3 kg/h. Stir until complete by gas chromatography. Quench the reaction with water (0.8 kg) and filter the reaction mixture and concentrate to afford 13.4 kg of the title compound. NMR (CDCl$_3$) 4.06 (m, 1H), 1.94 (s, 3H), 1.14 (d, 6H).

d. N-(4-Bromo-2,6-difluoro-phenyl)-N'-isopropyl-acetamidine

Add phosphoryl chloride (16.0 kg) to a mixture of 4-bromo-2,6-difluoro-phenylamine (14.5 kg), N-isopropyl acetamide (8.5 kg), TEA (10.6 kg) in toluene (115 kg) at <20° C. Stir at 10-20° C. until complete by HPLC. Remove the solvent under vacuum and add MtBE (64 kg). Adjust the pH of the mixture with 10% aq. sodium carbonate (250 kg). Filter the mixture and rinse the cake with MtBE (11×2 kg). Separate the phases and wash the aqueous layer with MtBE (22×2 kg). Combine the organic layers and concentrate, filter and wash with cyclohexane (0.6 kg) and dry to afford 17.2 kg of the title compound. MS (ES$^+$): m/z=292 (M+H)$^+$.

e. 6-Bromo-4-fluoro-1-isopropyl-2-methyl-1H-benzoimidazole

Add potassium tert-butoxide (6.9 kg) in portions to a solution of N-(4-bromo-2,6-difluoro-phenyl)-N'-isopropyl-acetamidine (16.2 kg) in N-methyl formamide (76 kg) while maintaining the temperature at T<30° C. Heat the mixture at 70-75° C. until complete by HPLC. Cool to 20-30° C. and quench by adding into water (227 kg) then extract with MtBE (37×4 kg). Wash the combined organic phases with brine (49×2 kg) and concentrate to 25-30 L, add n-hexane (64 kg) and filter the slurry to give 11 kg of the title compound. MS (ES$^+$): m/z=272 (M+H)$^+$.

Obtain additional purification by dissolving the crude compound in DCM and filtering through a silica gel and Celite® pad followed by isolation from an MtBE/hexane mixture.

f. 4-Fluoro-1-isopropyl-2-methyl-6-(4,4,5,5-tetramethyl-[1,3,2]dioxaborolan-2-yl)-1H-benzoimidazole Bubble nitrogen into a mixture of 6-bromo-4-fluoro-1-isopropyl-2-methyl-1H-benzoimidazole (600 g), bis(pinacolato)diboron (843 g), tricyclohexylphosphine (106 g), potassium acetate (652 g), and DMSO (3.6 L). Add palladium acetate (49 g) and heat at 100° C. until complete by HPLC. Cool the reaction mixture and dilute with water (18 L), then filter to isolate the solid. Dissolve the crude material in 1,2-dimethoxyethane (450 mL) and filter through Celite®. Use the filtrate directly in part g.

g. 6-(2-Chloro-5-fluoro-pyrimidin-4-yl)-4-fluoro-1-isopropyl-2-methyl-1H-benzoimidazole Bubble nitrogen into a mixture of 2,4-dichloro-5-fluoropyrimidine (517 g), sodium carbonate (586 g) in water (1.7 L) and 1,2-dimethoxyethane (3.4 L). Add bis(triphenylphosphine)palladium(II) chloride (4.9 g) and heat the reaction at 80±3° C. and add drop wise a solution of 4-fluoro-1-isopropyl-2-methyl-6-(4,4,5,5-tetramethyl-[1,3,2]dioxaborolan-2-yl)-1H-benzoimidazole in 1,2-dimethoxyethane from part f (5.1 L). Stir the mixture at 80±3° C. until complete by HPLC. Cool to RT and dilute with cold water (2.1 L, 5° C.). Stir for 1 hour then isolate the crude solid by filtration. Achieve further purification of the solid by trituration with IPA to give 472 g of the title compound. MS (ES$^+$): m/z=323 (M+H)$^+$.

h. [5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine Crystalline form III

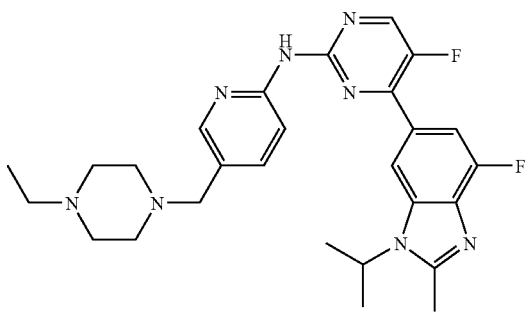

Bubble nitrogen into a mixture of 6-(2-chloro-5-fluoropyrimidin-4-yl)-4-fluoro-1-isopropyl-2-methyl-1H-benzoimidazole (465 g), 5-(4-ethyl-piperazin-1-ylmethyl)-pyridin-2-ylamine (321 g), potassium carbonate (403 g), 4,5-bis(diphenylphosphino)-9,9-dimethylxanthene (17 g) in t-amyl alcohol (2.3 L). Heat tris(dibenzylideneacetone) dipalladium (13.2 g) and the mixture at 100±5° C. until complete by HPLC. Cool to RT, dilute with DCM (1.2 L) and filter over a Celite® pad. Extract the filtrate with 4M HCl (2.3 L×2). Combine the aqueous layers and stir with charcoal (32 g). Filter through Celite®, add DCM (1.7 L) and adjust pH with NaOH (28% aq., 1.5 L). Collect the organic layer and wash the aqueous layer with DCM (1.7 L). Combine organic layers, wash with brine (1 L), and dry over magnesium sulphate. Use a solid supported Si-Thiol treatment to remove residual palladium and the solvent is exchanged to acetone. Filter the slurry and dry to give 605 g of crude product as Form I. Mix 605 g of Form I and 4.3 L of dry acetone. Slurry the suspension at 56-57° C. (reflux) for at least 18 hours and then at ambient temperature for 4 hours. Isolate the solid by vacuum filtration, producing a light yellow cake. Dry the solid in a vacuum oven at 35° C. until a constant weight of 570 g is obtained. Confirm the material by XRPD to be Form III of the title compound. MS (ES+): m/z=507 (M+H)$^+$.

The results of the following assays demonstrate evidence that the compounds exemplified herein are useful as specific CDK4/6 inhibitors and as anticancer agents. As used herein, "IC$_{50}$" refers to the concentration of an agent which produces 50% of the maximal inhibitory response possible for that agent and "EC$_{50}$" refers to the concentration of an agent which produces 50% of the maximal response possible for that agent.

CDK4 Inhibition Assay

To demonstrate that compounds included within the present invention exhibit affinity for CDK4 kinase, a CDK4 assay is performed. Functional assays provide support that the compounds of the present invention exhibit the ability to inhibit the CDK4 kinase activity. All ligands, radiolabels, solvents, and reagents employed in the following assays are readily available from commercial sources, or can be readily synthesized by one skilled in the art.

10 μL of test compound in 20% DMSO, 20 μL of adenosine 5'-triphosphate (ATP) and C-Terminal Retinoblastoma Fragment (CTRF) (Upstate cat # 12-439) solution, and 10 μL of enzyme solution are mixed in a 96 well plate. The ATP and CRTF solution is prepared from a mixture of 40 μM ATP, 0.16 μCi [$^{33}$P] ATP and 1 μM CTRF diluted in kinase buffer of 68 mM 4-(2-hydroxyethyl)-1-piperazineethanesulfonic acid (HEPES) pH 7.4, 6.72 mM MgCl$_2$, 6.72 mM dithiothreitol (DTT), and 0.013% TRITON™ X-100. The enzyme solution is prepared from 8 ng CDK4 enzyme (Proqinase cat # 0142-0373-1) diluted in the kinase buffer described above. Test compounds are serially diluted 1:3 in 20% DMSO to create a 10 point curve at a starting concentration of 20 μM. 20% DMSO buffer alone without added test compound is employed as a control, 500 mM ethylene diamine tetraacetic acid (EDTA) is used to determine the level of background $^{33}$P in the absence of enzyme activity. Reagents are mixed and incubated for 90 min at 20° C. The reaction is terminated by the addition of 80 μL 10% (v/v) H$_3$PO$_4$ and precipitation of material onto glass fibre filter plates (Millipore, MAFC N0B 50). The wells are washed four times with 0.5% H$_3$PO$_4$ and the radioactivity incorporated is determined with a microplate scintillation counter (Microbeta Trilux, Wallac).

The difference between the median value of high and low control is taken as 100% activity. A four parameter logistic curve fit is used to generate the IC$_{50}$ values using ActivityBase™ software (IDBS, Alameda Calif.). All the mesylate salts of the exemplified compounds display an IC$_{50}$ of <10 nM in the above assay. The compound of Example 25 has an IC$_{50}$ of 3 nM in the above assay. This demonstrates that the mesylate salts of the exemplified compounds are potent inhibitors of CDK4.

CDK6 Inhibition Assay

10 μL of test compound in 20% DMSO, 20 μL of ATP and CTRF (Upstate cat # 12-439) solution, and 10 μL of enzyme solution are mixed in a 96 well plate. The ATP and CRTF solution is prepared to give a final concentration of 100 μM ATP, 0.5 μCi [$^{33}$P]-ATP and 0.8 μM CTRF diluted in kinase buffer of 68 mM HEPES pH 7.4, 6.72 mM MgCl$_2$, 2.64 mM DTT, and 0.004% TRITON™ X-100. The enzyme solution is prepared for a final concentration of 1.7 ng/μL CDK6 enzyme (Proqinase cat # 7533) diluted in the kinase buffer described above in the CDK4 inhibition assay. Test compounds are serially diluted 1:3 in 20% DMSO to create a 10 point curve at a starting concentration of 20 μM. 20% DMSO buffer alone without added test compound is employed as a control, 500 mM EDTA is used to determine the level of background $^{33}$P in the absence of enzyme activity. Reagents are mixed and incubated for 90 min at 20° C. The reaction is terminated by the addition of 80 μL 10% (v/v) $H_3PO_4$ and precipitation of material onto glass fiber filter plates (Millipore, MAFC N0B 50). The wells are washed four times with 0.5% $H_3PO_4$ and the radioactivity incorporated is determined with a microplate scintillation counter (Microbeta Trilux, Wallac).

The data is analyzed in the same manner as for CDK4. Preferred exemplified compounds display an $IC_{50}$ of <30 nM in the above assay. The compound of Example 19 has an $IC_{50}$ of 5 nM in the above assay. This demonstrates that preferred exemplified compounds are potent inhibitors of CDK6.

Assay for Inhibition of PIM1 Kinase

Pim-1 (human, 0.46 nM final concentration) is incubated with 8 mM MOPS pH 7.0, 0.2 mM EDTA, 100 μM of an appropriate substrate peptide (see Pim-1 kinase inhibition assay protocol as described in Chen, L. S. et al. (2009) *Blood*, DOI: 10.1182/blood-2009-03-212852), 10 mM MgAcetate and [γ-$^{33}$P-ATP] (specific activity approx. 500 cpm/pmol, concentration as required). The reaction is initiated by the addition of the MgATP mix and then incubated for 40 minutes at room temperature. The reaction is stopped by the addition of 3% phosphoric acid solution. 10 μL of the reaction is then spotted onto a P30 filtermat and washed three times for 5 minutes in 75 mM phosphoric acid and once in methanol prior to drying and scintillation counting. For compound inhibition testing, compounds provided as 10 mM stocks in 100% DMSO are diluted 1:10 in 100% DMSO to give a 50× stock of the top concentration of the curve. The 50× stock is then serially diluted 1:3 in 100% DMSO to create a 10 point concentration-response curve and diluted 1:50 (20 μM to 0.001 μM final in 2% final DMSO concentration) in the reaction mixture to determine compound activity. Control wells contain DMSO only while the baseline is established in control wells acid-stopped at time 0 minutes. The percent inhibition determined from the controls on each plate and ten-point compound concentration data were then fit to a four-parameter logistic equation using ACTIVITYBASE 4.0.

Preferred exemplified compounds display an $IC_{50}$ of <0.01 μM. The compound of Example 25 has an $IC_{50}$ of 0.003 μM in the assay described above. This demonstrates that preferred exemplified compounds are potent inhibitors of Pim-1 kinase.

Solubility Assay

The appropriate amounts of test compound are weighed into separate chromatographic vials. The required volume of 0.05M Phosphate buffer, pH 8.0 (dissolve 6.7 g of Sodium Phosphate Dibasic X 7$H_2O$ in 500 mL of HPLC grade water, adjust to pH 8.0 with Phosphoric Acid 85%) is added to the sample vial to achieve a target concentration of 2.0 mg/mL. An appropriate standard solution in DMSO is prepared by adding the required volume of DMSO to the standard vial to achieve a target concentration of 2.0 mg/mL. The vials are capped securely and placed in a rotation device. The vials are rotated through 360° for at least 16 hours at ambient temperature with an angular speed of about 50 rpm. A visual examination of the individual vials is performed after rotation. 250 μL from each vial is filtered through a 0.7 μm glass filter. The sample filtrate and standard filtrate are collected into separate wells of 96 deep well plates. A dilution series is prepared (2000 μg/mL, 200 μg/mL, 20 μg/mL 2.0 μg/mL plus a blank DMSO sample) by appropriate serial dilution in DMSO of the 2.0 mg/ml standard solution.

The sample and standard solutions are analysed by HPLC (LC Column: XTerra MS, C18, 2.1×50 mm, 3.5 μm, at 50° C.; mobile phases: A—0.2% Formic Acid in Water; B—0.2% Formic Acid in acetonitrile; Gradient: 5-100% B in 3 min, hold at 100% B for 0.5 min; flow rate: 750 μL/min; injection volume: 1 μL; Diode array detector scan from 200 nm to 400 nm. The wavelength extracted and used for quantitation is selected to provide the most accurate estimation of the sample preparations.) Retention time used for peak assignment for the test compound is obtained from the 200 μg/mL standard preparation chromatogram.

Solubility values are calculated using a four-level calibration curve. The line of best fit for peak area of calibration standards calculated by chromatographic management data system using linear or quadratic through zero fit is used. Solubility results are reported in mg/mL. Preferred exemplified compounds display a solubility of at least 2 mg/ml in pH 8 phosphate buffer using the above assay. The compound of Example 16 displays a solubility of 2.099 mg/ml in pH 8 phosphate buffer using the above assay. This data thus demonstrates that preferred exemplified compounds of the invention are readily soluble in an aqueous solution.

Rat Oral Bioavailability Assay

Male Sprague Dawley rats (body weight range 250-320 g) with indwelling femoral arterial cannulae are obtained from Charles River, Wilmington, Mass. 01887, USA. Test compound is administered intravenously in solution (2 mL/kg) in: 10% N-methyl pyrollidone/18% Captisol® in 22.5 mM phosphate buffer, pH 3. The final drug concentration is 0.25 mg/mL (free base equivalents). Blood samples are obtained using the indwelling cannula over 24 h. The animals are then administered an oral dose of test compound in suspension (5 mL/kg) in 1% w/v hydroxyethylcellulose/0.25% v/v polysorbate 80/0.05% v/v antifoam in purified water. The final drug concentration is 0.2 mg/mL (free base equivalents). Further blood samples are collected via the indwelling cannula over 24 h. Samples of plasma were obtained by centrifugation and stored frozen (−20° C.) prior to analysis.

An internal standard compound (for normalisation) in acetonitrile/methanol (1:1, v/v) is added to samples of plasma to precipitate protein and the samples are centrifuged prior to analysis. The supernatants are analysed by injection and rapid gradient elution on a Javelin Betasil C18 column (20×2.1 mm cartridge, Mobile phase A: Water/1 M ammonium bicarbonate, 2000:10 v/v, Mobile Phase B: MeOH/1 M ammonium bicarbonate, 2000:10 v/v). The eluted analytes are detected by LC-MS-MS analysis using a Sciex API 4000 triple quadrupole mass spectrometer. Concentrations of compounds in plasma are determined from standards prepared under identical conditions.

The oral bioavailability is obtained by dividing the area under the plasma concentration time curve after oral administration by the area under the curve following intravenous administration (after normalising for dose administered). Results are presented as Fraction bioavailable relative to the intravenous dose (% F). Preferred exemplified compounds display a % F value of >20% in the above-mentioned assay. The compound of Example 22 displays a % F value of 48.5% in the above-mentioned assay. This demonstrates that preferred exemplified compounds have good oral bioavailability.

Inhibition of Phosphorylation of Retinoblastoma Protein (pRb) and DNA Content Assay COLO 205 Cells from the American Type Culture Collection (ATCC) are plated at 2000 cells/well in 96 well Beckman Dickinson BIOCOAT™ plates, and are incubated in RPMI 1640 medium (e.g., GIBCO, catalog #52400-025) with 10% Fetal Bovine Serum (FBS e.g. Gibco cat #11000-144) and 1% sodium pyruvate (Gibco catalog #11360-070) in 37° C., 5% $CO_2$ for 24 h. Cells are treated by adding test compound to the medium, dosing at 10 points of 1:3 dilutions across the range of 20 µM to 0.001 µM, and with final DMSO concentration at 0.25%. After 24 h exposure to the compounds, cells are fixed with the PREFER™ fixative [Anatech LTD., Cat # 414] for 30 min at RT, then are permeabilized with 0.1% TRITON® X100 in phosphate buffered saline (PBS) solution for 15 min at RT. Cells are washed twice with PBS then digested with 50 µg/mL RNAse (Ribonuclease A, Sigma cat # R-6513) in 37° C. incubator for 60 min. Fixed cells are blocked with 1% bovine serum albumin (BSA, Amersham cat #RPN412V) for 30 min. Primary antibody, anti-phosphoRB purified mouse monoclonal antibody (BD Pharmigen cat # 558385), is added at 1:2000 in PBS with 1% BSA to the cells and incubated overnight at 4° C. After 3 PBS washes, cells are incubated with Alexa488 labelled secondary antibody, goat anti mouse IgG Alexa 488 (Invitrogen cat #A11017) for 1 h at RT. Again they are washed 3 times with PBS, and then 15 µM propidium iodide (1:100 dilution with PBS from the original solution, Invitrogen cat #P3566) is added to stain nuclei. Fluorescence plates are scanned with ACUMEN EXPLORER™ [Laser-scanning fluorescence microplate cytometer (comprising of 488 nm argon ion laser excitation and multiple photomultiplier tube detection), manufactured by TTP LABTECH LTD] to measure phosphorylation of Rb protein and DNA content. Image analysis is based on cellular fluorescent signals for identifying cells in different subpopulations. Assay outputs are percentage of each identified subpopulations, % phosphoRB positive, % 2 N and % 4 N. The $IC_{50}$ and $EC_{50}$ values are determined by curve fitting to a four parameter logistic for each output using ACTIVITY BASE™. All the mesylate salts of the exemplified compounds display an $IC_{50}$ of <200 nM in the above assay. The compound of Example 25 has activity of about 100 nM in the above assay. This demonstrates that the mesylate salts of the exemplified compounds are potent inhibitors of CDK4/6 kinase activity (as measured by a low level of phosphorylation of pRb) in an in vitro whole cell based assay.

Further, all the mesylate salts of the exemplified compounds are able to induce specific arrest in the G1 phase of the cell cycle even when present at concentrations of at least 2 µM. Specific G1 arrest is indicated by >90% of cells having a 2N genotype. Specific G1 arrest even at physiologically relevant concentrations of active compound demonstrates that the compounds of the invention are specific inhibitors of CDK4/6 and that non-specific inhibition of other Cdks is minimised, which would result in cell cycle arrest in other phases.

Human Subcutaneous Xenograft Models

Human colorectal cancer cells (colo-205), human acute myeloid leukaemia (AML) cells (MV4-11), human glioblastoma cells (U87MG), and human lung cancer cells (NCI H460 and calu 6) are expanded in culture (colo-205 and NCI H460 are grown in RPMI 1640 media with L-glutamine, 25 mM HEPES, 1 mM Na pyruvate, 10% FBS; MV4-11 is grown in Iscove's modified Dulbecco's media with L-glutamine, 25 mM HEPES, 10% FBS; U87MG and calu 6 are grown in Eagle's MEM with Earle Salts, L-glutamine and non essential amino acids, 1 mM Na pyruvate and 10% FBS harvested (colo-205, U87-MG, calu 6 and NCI-H460 trypsinized (Invitrogen catalog 25200-056); MV4-11 by centrifugation), and injected subcutaneously (5 million cells/animal mixed 1:1 in Matrigel, BD Biosciences) onto the rear flank of athymic nude mice. Test compound is prepared in an appropriate vehicle (1% hydroxyethyl cellulose, in 25 mM phosphate buffer pH 2) and is administered by oral gavage daily (at 25, 50 or 100 mg/kg (mpk)) for 21 days when tumours are established (11-29 days after implant). Tumour response is determined by tumour volume measurement performed twice a week during the course of treatment.

The statistical method for assessing Tumour Growth Delay (TGD-Individual interpolation method) is as follows: For each animal, the time to reach a specified tumour volume (threshold) is calculated by interpolating between the last measurement before reaching the threshold and the next measurement. The interpolation is linear using $\log_{10}$(volume) vs. time. If an animal never reaches the threshold, its crossing time is reported at ">T" where T is the last day measured for that animal. These crossing times are analyzed as "time-to-event" data with right-censoring using a Weibull distribution. A mean and standard deviation are determined for each treatment group. Tumour growth delay (TGD) is the difference in mean crossing time between a treated group and the vehicle control group. T-tests are performed using the means and standard deviations from the Weibull analysis. Body weight is taken as a general measurement of toxicity.

Following a protocol essentially as described above, the compound of Example 16 demonstrates anti-tumour activity in these models as shown in Table 3, thus demonstrating that the compound of Example 16 has potent in vivo activity against a range of $Rb^+$ tumours.

Further, in the AML MV4-11 xenografts, tumour regression is observed at a dose of 100 mg per Kg (mpk), indicative of the proapoptotic Pim-1 inhibitory activity of the compound of Example 16, see Table 4.

TABLE 3

Tumour Growth Delay in different human xenograft models

| Xenograft | Dose | TGD Days (750 m3) | SE |
| --- | --- | --- | --- |
| colo-205 | 100 mpk | 39.9 | 4.6 |
|  | 50 mpk | 17.4 | 3.2 |
|  | 25 mpk | 15.3 | 3.8 |
| MV4-11 | 100 mpk | 28.8 | 1.1 |
|  | 50 mpk | 11.5 | 4.0 |
|  | 25 mpk | 10.4 | 4.7 |
| U87 MG | 100 mpk | 21.4 | 2.7 |
|  | 50 mpk | 10.0 | 2.2 |
|  | 25 mpk | 6.1 | 3.2 |
| H460 | 100 mpk | 6.7 | 2.7 |
|  | 50 mpk | 4.0 | 4.2 |
|  | 25 mpk | 1.5 | 1.8 |

TABLE 4

Anti tumour activity of the compound of Example 16 in the MV4-11 model

| Treatment | Tumor volume (mg) at start of dosing period (day 28) | SE (mg) | p value | Tumor volume (mg) at end of dosing period (day 49) | SE (mg) | p value |
|---|---|---|---|---|---|---|
| Vehicle, 0.2 ml, PO, dose qdx21/ 1% HEC + 0.1% AF in 25 mM PB pH 2 | 219.45 | 17.42 | Ctrl | 1271.15 | 100.9 | Ctrl |
| Compound of example 16, 100 mpk, PO, dose qdx21 | 225.94 | 29.61 | NS | 116.68 | 15.29 | *** |

Tumor volume measurements. P value is the statistical significance compared to vehicle control group (Ctrl) on day of measurement- NS, not significant; ***: p <= 0.001.

Orthotopic Brain Xenograft Model

In vivo brain tumour model: Male NIH-RNU rats weighing between 225 and 300 g are anesthetized with isoflurane and placed into a stereotaxic frame (David Kopf Instruments, Tujunga, Calif.). A mid-line incision is made and a 1 mm burr hole drilled 2 mm lateral from the midline and 3 mm anterior to the coronal suture. A cell suspension of $5 \times 10^5$ U87 MG human glioblastoma tumour cells (grown in Eagle's MEM with Earle Salts, L-glutamine and non essential amino acids, 1 mM Na pyruvate and 10% FBS) in 10 µL ($5 \times 10^5$ cells for qd dosing and $1 \times 10^6$ for q2d dosing) is injected at a depth of 3 mm by means of a 25 or 50 µl Hamilton syringe over a period of approximately 2 min using a stereotaxic-mounted syringe pump (Nano-Injector, model #53310 and Stereotaxic Adapter Clamp, part #51681, Stoelting Co, Wood Dale, Ill.) with the syringe left in place for an additional 1 min to prevent back-flow and the syringe is slowly withdrawn. The hole is sealed with bone wax, the operative field washed with saline solution and the incision closed with sutures or wound clips.

Test compound is formulated in vehicle (1% w/v hydroxy-ethylcellulose/0.25% v/v polysorbate 80/0.05% v/v antifoam in purified water) and administered every day for 21 days at 20, 40 and 80 mpk (qdx21) and 80 mpk q2dx10 starting on day 4 after tumour implant.

The primary outcome variable is survival. Animals are monitored daily until death and, in consultation with the veterinary staff and in adherence with the policy on tumour implantation, euthanized if the animal becomes moribund. The cells are implanted in the frontal lobe in order to minimize potential brain dysfunction such as motor deficits and control of vital functions. Frontal lobe tumours in humans are said to be "silent," that is the most common presenting symptoms include headache, nausea, vomiting, and cognitive deficits. Morbidity is therefore most likely to manifest as lethargy and loss of body weight. Survival data are analyzed by the Kaplan-Meier method for median survival analysis using JMP v6.0.2 (SAS Institute).

Following a protocol essentially as described above, the compound of Example 16 resulted in a statistically significant increase in median survival (when compared to vehicle treated animals) at the following doses; 40 mpk qd, 80 mpk qd and 80 mpk q2d, (see Table 5) thus demonstrating that the compound of Example 16 is able to cross the blood-brain barrier and have potent in vivo inhibitory activity in an orthotopic glioblastoma tumour xenograft model.

TABLE 5

Mean & Median survival (days) resulting from administration of compound of Example 16.

| Treatment Group | Mean Survival (days) | Std Error (days) | p value Log-rank | Median Survival (days) |
|---|---|---|---|---|
| Vehicle PO qd | 25.1 | 2.8 | — | 27 |
| PO 20 mg/kg qd | 29.8 | 0.7 | 0.5 | 31 |
| PO 40 mg/kg qd | 34.3 | 1.7 | 0.0316 | 37 |
| PO 80 mg/kg qd | 36.9 | 1.3 | 0.0006 | 37 |
| Vehicle PO q2d | 23.0 | 3.5 | — | 24 |
| PO 80 mg/kg q2d | 33.0 | 1.2 | 0.0295 | 34 |

In a separate experiment, to determine compound plasma and brain exposure levels, non-tumour bearing male Sprague Dawley rats are administered a single dose of the compound of Example 16 orally at 30 mg/kg. Samples are taken over 48 h in order to determine plasma and brain concentrations. Animals are sacrificed, and whole blood collected by cardiac puncture and plasma isolated by centrifugation. Whole brain is collected and snapped frozen in liquid nitrogen.

Samples of brain are prepared by homogenization in 80% methanol/20% $H_2O$. An internal standard compound in acetonitrile/methanol (1:1, v/v) is added to samples of plasma or brain homogenate to precipitate protein and the samples are centrifuged prior to analysis. The supernatants are analysed by injection and rapid gradient elution on a Javelin Betasil C18 column (20×2.1 mm cartridge, Mobile phase A: Water/1 M $NH_4HCO_3$, 2000:10 v/v, Mobile Phase B: MeOH/1 M $NH_4HCO_3$, 2000:10 v/v). The eluted analytes are detected by LC-MS-MS analysis using a Sciex API 4000 triple quadrupole mass spectrometer. Concentrations of compounds in plasma or brain are determined from standards prepared under identical conditions.

The plasma and brain concentrations are determined in this study from a group of three rats at each time point (see Tables 6a and 6b) and are used to calculate the area under the plasma concentration/time curve or the brain concentration/time curve from 0 to 48 hours. Examination of the ratio of exposure in brain either using the area under the curve (AUC) or maximum plasma and brain concentrations (Cmax), see Table 6c, demonstrates that the compound distributes well into brain with a brain/plasma ratio of approximately 1. Maximal concentrations (Tmax) are detected at 4 h. These experiments demonstrate that the compound of Example 16 is able to cross the blood-brain barrier and distributes well into the brain.

TABLE 6a

Plasma concentrations of the compound of Example 16 (ng/mL) determined in male SD Rats

| | Time (h) | | | |
|---|---|---|---|---|
| | 2 | 4 | 24 | 48 |
| Mean | 1014 | 1504 | 1018 | 972.0 |
| S.D. | 288.0 | 134.8 | 236.2 | 666.0 |
| % CV | 28.4 | 9.0 | 23.2 | 68.5 |
| n | 3 | 3 | 3 | 3 |

TABLE 6b

Brain concentrations of the compound of Example 16 (ng/g) determined in male SD Rats

| | Time (h) | | | |
|---|---|---|---|---|
| | 2 | 4 | 24 | 48 |
| Mean | 758.5 | 1500 | 992.4 | 718.0 |
| S.D. | 82.38 | 268.9 | 54.83 | 232.0 |
| % CV | 10.86 | 17.93 | 5.525 | 32.31 |
| n | 3 | 3 | 3 | 3 |

TABLE 6c

Mean exposure to the compound of Example 16 in plasma and brain determined in male SD Rats

| Parameter | Units | Plasma | Brain | Brain/Plasma Ratio |
|---|---|---|---|---|
| AUC | ng * Hours/mL or ng * Hours/g | 52300 | 47900 | 0.92 |
| AUC Interval | | (0-48 Hours) | (0-48 Hours) | |
| Cmax | ng/mL or ng/g | 1500 | 1500 | 1.0 |
| Tmax | Hours | 4.00 | 4.00 | |

Combination Studies with Temozolomide

U87 MG subcutaneous xenografts are grown and measured as previously described. The compound of Example 16 is formulated and administered as previously described and dosed orally once a day from days 11-31. Temozolomide (Schering Corporation) is formulated in 1% w/v hydroxyethylcellulose/0.25% v/v polysorbate 80 in purified water and administered by interperitoneal injection on days 11 and 18. A comparison of the single agent activity of temozolomide with a combination treatment with the compound of Example 16 is shown in Table 7. Tumor growth is analyzed by 2-way interaction analysis; log-transformed tumor volumes were analyzed with a repeated measures analysis of variance (ANOVA) using a spatial power correlation model in SAS, version 9.1 (Cary, N.C.). A 2×2 factorial structure was used to estimate the treatment effects and the interaction effect between the two treatments. The interaction effect was tested across all time points ("overall" test) and at each time point. The increased inhibition of tumour growth seen in the combination groups compared to those receiving temozolomide alone indicates that temozolomide and the compound of Example 16 demonstrate potent in vivo anti-tumour activity in combination in a subcutaneous glioblastoma tumour xenograft model.

TABLE 7

U87-MG Xenograft Study Combination of Compound of Example 16 and Temozolomide

| | Tumor volume (mg) | | |
|---|---|---|---|
| Treatment | at end of dosing period (day 31) | SE (mg) | p value |
| Vehicle, 0.2 ml, PO, qdx21/1% HEC + 0.1% AF in 25 mM PB pH 2 | 456.54 | 169.3 | Ctrl |
| Temozolomide, 3 mpk, IP, q7dx2 | 101.88 | 44.16 | ** |
| Compound of example 16, 50 mpk, PO, qdx21/temozolomide, 3 mpk, IP, q7dx2 | 30.22 | 7.57 | *** |

Tumor volume measurements. P value is the statistical significance compared to vehicle control group (Ctrl) on day of measurement-

**: $0.001 < p <= 0.01$;

***: $p <= 0.001$.

U87 MG orthotopic brain xenografts are grown and survival measured as previously described. Groups of animals are treated with temolozomide (TMZ), or a combination of Example 16 (every day or every other day dosing) plus temozolomide. As shown in Table 8, the increase in mean survival in the combination groups compared to those receiving temozolomide alone indicates that temozolomide and the compound of Example 16 have potent in vivo inhibitory activity in combination in an orthotopic glioblastoma tumour xenograft model. The absence of mortality and loss of body weight (see Table 9) for the combination treatments indicate that they are well tolerated and that there are no overlapping toxicities.

TABLE 8

Mean & Median survival (days) resulting from administration of compound of Example 16 in combination with Temozolomide.

| Treatment Group | Mean Survival (days) | Std Error (days) | p value Log-rank | Median Survival (days) |
|---|---|---|---|---|
| Vehicle PO 1 mL/kg qdx20 | 28.1 | 1.9 | — | 30 |
| Temozolomide (TMZ) IP 3 mg/kg (days 6 and 13) | 46.9 | 3.3 | <0.0001 | 47 |
| Compound of example 16 40 mg/kg qdx20 + TMZ IP 3 mg/kg (Days 6 & 13) | 60.1 | 3.6 | 0.0002 | 61 |
| Compound of example 16 40 mg/kg q2dx10 + TMZ IP 3 mg/kg (Days 6 &13) | 70.5 | 4.4 | 0.0032 | 70 |

TABLE 9

Mortality and body weight of animals from the temozolomide/compound of Example 16 study

| Treatment | Maximum body weight loss (%) | Dead/total animals |
|---|---|---|
| Vehicle, 0.2 ml, PO, qdx21/1% HEC + 0.1% AF in 25 mM PB pH 2 | 0 | 0/8 |
| Temozolomide, 3 mpk, IP, q7dx2 | −1 | 0/8 |
| Compound of example 16, 50 mpk, PO, qdx21/temozolomide, 3 mpk, IP, q7dx2 | −1 | 0/8 |

Combination Studies with Gemcitabine

Calu-6 (lung) subcutaneous xenografts are grown and measured as previously described. Gemcitabine was formulated in saline (0.9% sodium chloride in purified water) and administered via intraperitoneal injection q3dx7. Test compound was administered qdx21. A comparison of the single agent activity of gemcitabine with combination treatments containing both gemcitabine and the compound of Example 16 are shown in Table 10. Tumour growth is analyzed by 2-way interaction analysis. The increased inhibition of tumour growth seen in the combination groups compared to those receiving gemcitabine indicates that the drugs demonstrate potent in vivo anti-tumour activity in combination in a subcutaneous lung cancer xenograft model. The low incidence of mortality and loss of body weight for the combination treatments indicate they are well tolerated and suggest no overlapping toxicities (see Table 11).

TABLE 10

Calu-6 xenograft study combination of compound of example 16 and gemcitabine

| Treatment | Tumor volume (mg) at end of dosing period (day 38) | SE (mg) | p value |
|---|---|---|---|
| Vehicle, 1% HEC in 25 mM PB pH 2, 0.2 ml, PO, qdx21/saline, 0.2 ml, IP, q3dx7 | 949.73 | 202.66 | Ctrl |
| Gemcitabine, 60 mpk, IP, q3dx7 | 509.18 | 64.89 | ** |
| Compound of example 16, 50 mpk, PO, qdx21/Gemcitabine, 60 mpk, IP, q3dx7 | 234.94 | 30.86 | *** |

Tumor volume measurements. P value is the statistical significance compared to vehicle control group (Ctrl) on day of measurement-
**: $0.001 < p <= 0.01$;
***: $p <= 0.001$.

TABLE 11

Mortality and body weight of animals from the gemcitabine/compound of Example 16 study

| Treatment | Maximum body weight loss (%) | Dead/total animals |
|---|---|---|
| Vehicle, 1% HEC in 25 mM PB pH 2, 0.2 ml, PO, qdx21/saline, 0.2 ml, IP, q3dx7 | 0 | 0/7 |
| Compound of example 16, 50 mpk, PO, qdx21/Gemcitabine, 60 mpk, IP, q3dx7 | −14 | 1/7 |
| Gemcitabine, 60 mpk, IP, q3dx7 | −12 | 0/7 |

Oral administration of the compounds of the present invention is preferred. Intravenous administration of the compounds of the present invention is also preferred. Depending on the circumstances, other routes of administration may be used or even preferred. For example, transdermal administration may be very desirable for patients who are forgetful or petulant about taking oral medicine. Compounds of the present invention may also be administered by the percutaneous, intramuscular, intranasal or intrarectal route in particular circumstances. The route of administration may be varied in any way, limited by the physical properties of the drugs, the convenience of the patient and the caregiver, and other relevant circumstances (*Remington's Pharmaceutical Sciences*, 18th Edition, Mack Publishing Co. (1990)).

The invention claimed is:
1. A compound of formula (I):

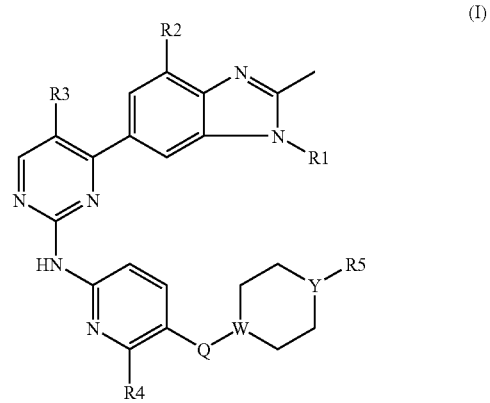

wherein,

R1 is $C_3$-$C_5$ alkyl, $C_3$-$C_5$ cycloalkyl or cyclopropyl-methyl;

R2 and R3 are H or fluorine, wherein at least one of R2 or R3 is fluorine;

R4 is H or $CH_3$;

R5 is $C_1$-$C_6$ alkyl or —NR6R7 wherein R6 and R7 are each $C_1$-$C_3$ alkyl;

Q is $CH_2$, O, S or a direct bond;

and

W and Y are C or N, wherein at least one of W or Y is N and wherein when Q is O or S, W is C;

or a pharmaceutically acceptable salt thereof.

2. The compound according to claim 1, or a pharmaceutically acceptable salt thereof, wherein R1 is isopropyl, cyclopropyl, cyclopentyl or cyclopropyl-methyl.

3. The compound according to claim 2, or a pharmaceutically acceptable salt thereof, wherein R1 is isopropyl.

4. The compound according to claim 3, or a pharmaceutically acceptable salt thereof, wherein R2 and R3 are each fluorine.

5. The compound according to claim 4, or a pharmaceutically acceptable salt thereof, wherein R5 is $C_1$-$C_3$ alkyl.

6. The compound according to claim 2, or a pharmaceutically acceptable salt thereof, wherein R5 is —NR6R7 wherein R6 and R7 are each ethyl.

7. The compound according to claim 5, or a pharmaceutically acceptable salt thereof, wherein Q is $CH_2$ or a direct bond.

8. The compound according to claim 7, or a pharmaceutically acceptable salt thereof, wherein Y is N.

9. The compound according to claim 8, or a pharmaceutically acceptable salt thereof, wherein R4 is H.

10. The compound according to claim 9, or a pharmaceutically acceptable salt thereof, wherein Q is $CH_2$.

11. The compound according to claim 10, or a pharmaceutically acceptable salt thereof, wherein W is N.

12. The compound according to claim 11 which is:

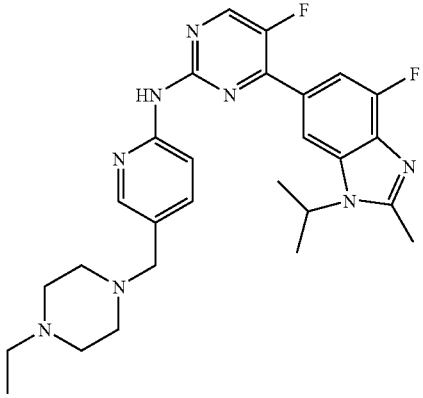

or a pharmaceutically acceptable salt thereof.

13. The compound according to claim 12 which is the mesylate salt.

14. [5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine crystalline form III, characterised by an X-ray powder diffraction pattern (CuKα radiation, λ=1.54056 Å) comprising a peak at 21.29 (2θ±0.1°) and optionally one or more peaks selected from the group comprising 11.54, 10.91, and 12.13 (2θ±0.1°).

15. [5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine crystalline form III as claimed in claim 14 which is further characterised by a $^{13}$C NMR spectrum comprising chemical shift peaks ν(F1) [ppm] at 112.7, 127.3 and 129.4.

16. The compound according to claim 1, or a pharmaceutically acceptable salt thereof, selected from the group consisting of:

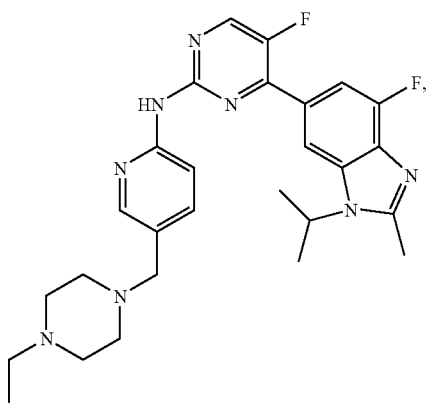

-continued

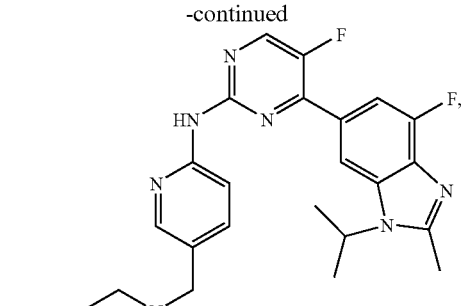

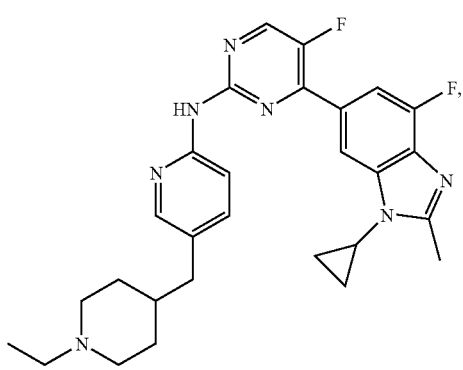

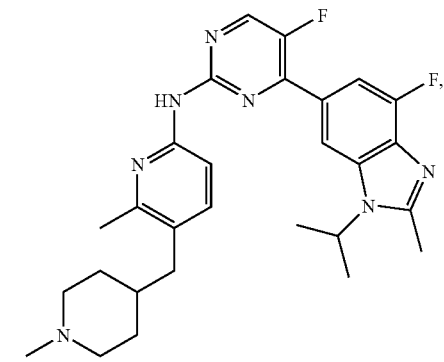

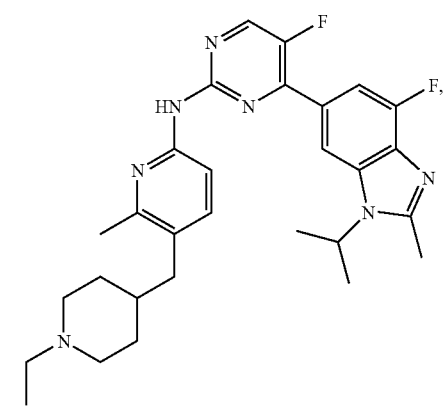

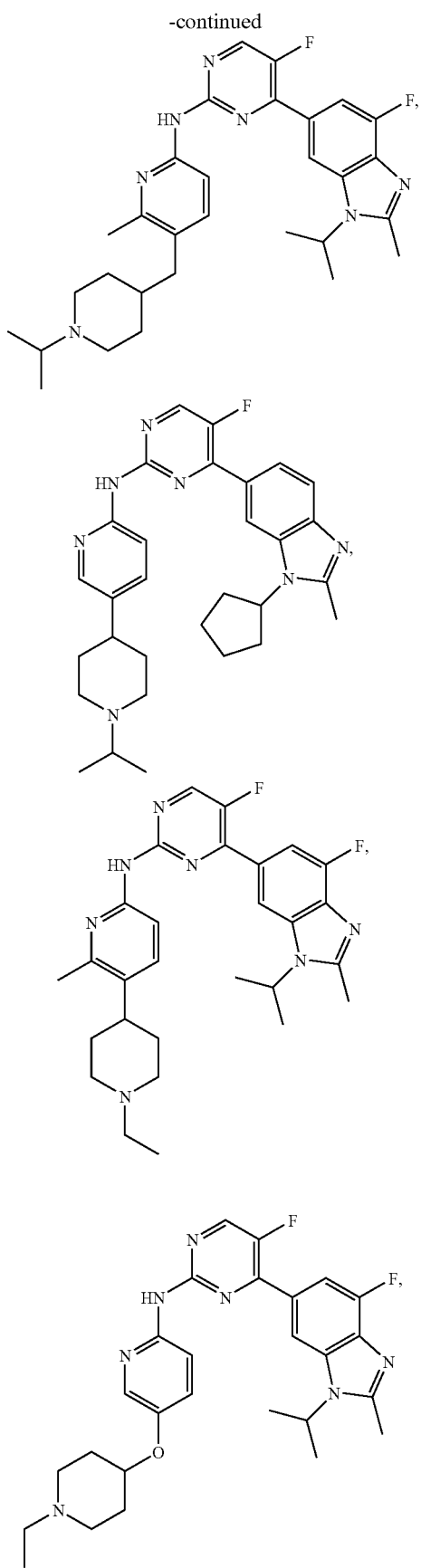
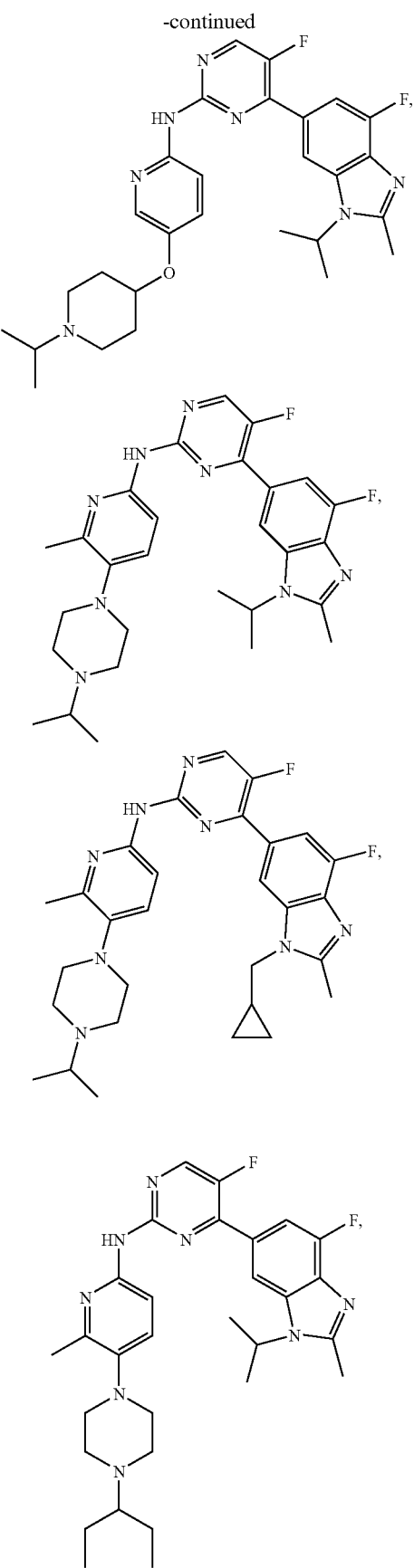

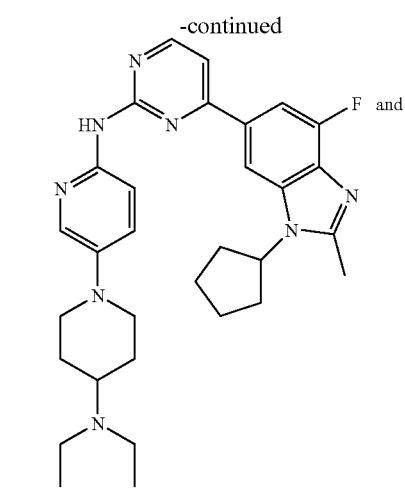

17. A pharmaceutical formulation comprising a compound of formula (I):

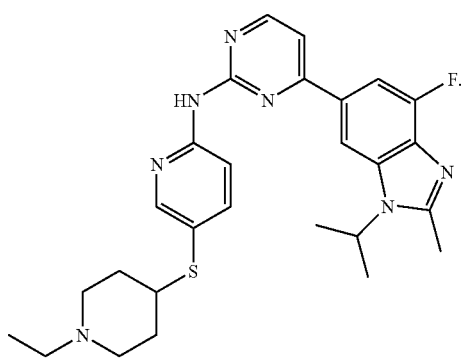

wherein,

R1 is $C_3$-$C_5$ alkyl, $C_3$-$C_5$ cycloalkyl or cyclopropyl-methyl;

R2 and R3 are H or fluorine, wherein at least one of R2 or R3 is fluorine;

R4 is H or $CH_3$;

R5 is $C_1$-$C_6$ alkyl or —NR6R7 wherein R6 and R7 are $C_1$-$C_3$ alkyl;

Q is $CH_2$, O, S or a direct bond;

and

W and Y are C or N, wherein at least one of W or Y is N and wherein when Q is O or S, W is C;

or a pharmaceutically acceptable salt thereof, and a pharmaceutically acceptable carrier, diluent or excipient.

18. The pharmaceutical formulation according to claim 17 comprising the compound of formula (I) wherein, R1 is isopropyl, R2 and R3 are each fluorine, R5 is $C_1$-$C_3$ alkyl, and Q is $CH_2$ or a direct bond, or a pharmaceutically acceptable salt thereof.

19. The pharmaceutical formulation according to claim 18 comprising the compound which is:

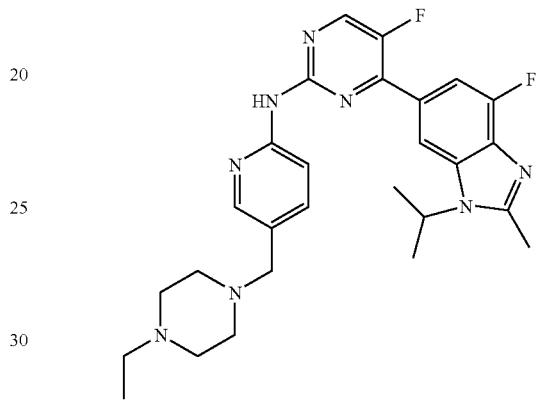

or a pharmaceutically acceptable salt thereof.

20. The pharmaceutical formulation according to claim 17 comprising the compound which is [5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine crystalline form III, characterised by an X-ray powder diffraction pattern (CuKα radiation, λ=1.54056 Å) comprising a peak at 21.29 (2θ±0.1°) and optionally one or more peaks selected from the group comprising 11.54, 10.91, and 12.13 (2θ±0.1°), or a pharmaceutically acceptable salt thereof.

21. A method of treating cancer selected from the group consisting of colorectal cancer, breast cancer, lung cancer, prostate cancer, glioblastoma, mantel cell lymphoma, chronic myeloid leukaemia and acute myeloid leukaemia in a mammal comprising administering to a mammal in need of such treatment an effective amount of a compound of formula (I):

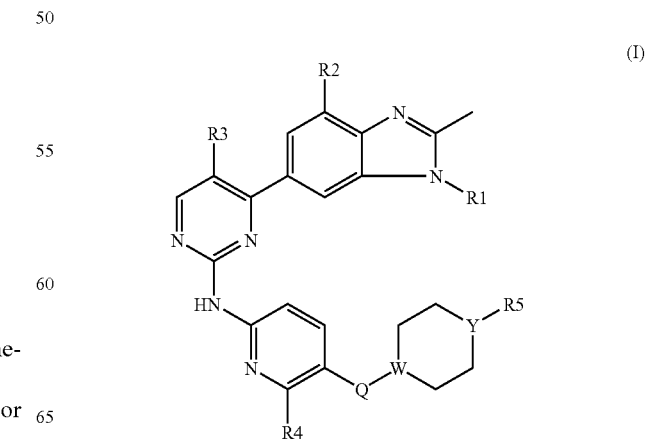

wherein,

R1 is C₃-C₅ alkyl, C₃-C₅ cycloalkyl or cyclopropyl-methyl;

R2 and R3 are H or fluorine, wherein at least one of R2 or R3 is fluorine;

R4 is H or CH₃;

R5 is C₁-C₆ alkyl or —NR6R7 wherein R6 and R7 are C₁-C₃ alkyl;

Q is CH₂, O, S or a direct bond;

and

W and Y are C or N, wherein at least one of W or Y is N and wherein when Q is O or S, W is C;

or a pharmaceutically acceptable salt thereof.

22. The method according to claim 21 comprising the compound of formula (I) wherein, R1 is isopropyl, R2 and R3 are each fluorine, R5 is C₁-C₃ alkyl, and Q is CH₂ or a direct bond, or a pharmaceutically acceptable salt thereof.

23. The method according to claim 22 comprising the compound which is:

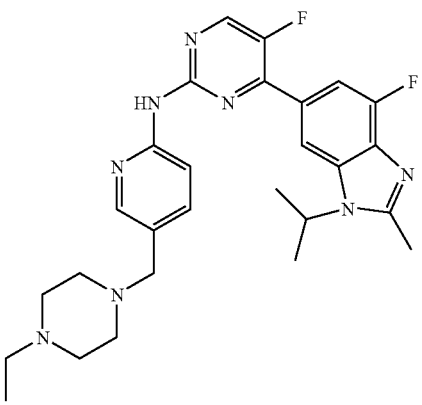

or a pharmaceutically acceptable salt thereof.

* * * * *

UNITED STATES PATENT AND TRADEMARK OFFICE
CERTIFICATE OF CORRECTION

PATENT NO. : 7,855,211 B2  Page 1 of 1
APPLICATION NO. : 12/637789
DATED : December 21, 2010
INVENTOR(S) : David A. Coates et al.

It is certified that error appears in the above-identified patent and that said Letters Patent is hereby corrected as shown below:

Column 46, Table 3, delete "750 m3" and insert -- 750 $mm^3$ --, therefor.

Signed and Sealed this
Thirteenth Day of September, 2011

David J. Kappos
*Director of the United States Patent and Trademark Office*

UNITED STATES PATENT AND TRADEMARK OFFICE
CERTIFICATE OF CORRECTION

PATENT NO. : 7,855,211 B2
APPLICATION NO. : 12/637789
DATED : December 21, 2010
INVENTOR(S) : David Andrew Coates et al.

It is certified that error appears in the above-identified patent and that said Letters Patent is hereby corrected as shown below:

In the Specification

In Column 17, Line 11: Delete "biss" and insert -- bis --, therefor.

In Column 17, Line 66: Delete "dicyclohexylphosphino)" and insert -- 2-(dicyclohexylphosphino) --, therefor.

In Column 24, prep 60: Delete "piperidin-4-ylmethyl-pyridin- piperidin-4-ylmethyl-pyridin-" and insert -- piperidin-4-ylmethyl-pyridin- --, therefor.

In Column 30, example 6: Delete "pyrimdiin-2-yl" and insert -- pyrimidin-2-yl --, therefor.

In Column 35, Line 28: Delete "methanosulfonic acid" and insert -- methanesulfonic acid --, therefor.

Signed and Sealed this
Fourteenth Day of July, 2020

Andrei Iancu
*Director of the United States Patent and Trademark Office*

CERTIFICATE OF CORRECTION (continued)
U.S. Pat. No. 7,855,211 B2

In the Claims

Column 56, Lines 50-65, in Claim 16: Delete " 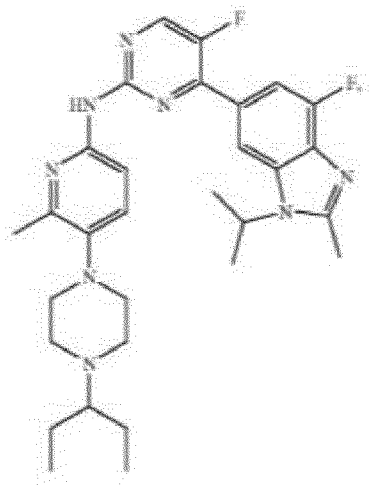 ; " and insert

-- 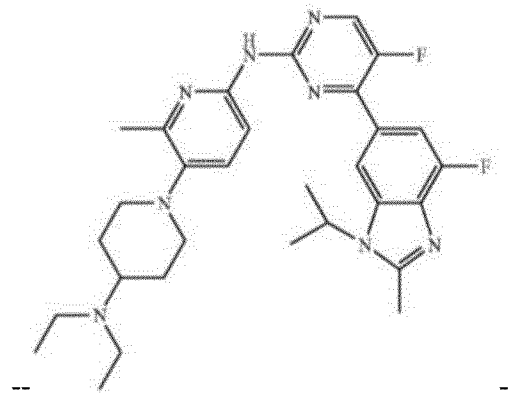 --, therefor.